US009649047B1

United States Patent
Damadian et al.

(10) Patent No.: US 9,649,047 B1
(45) Date of Patent: May 16, 2017

(54) MONITORING AND TREATMENT OF MULTIPLE SCLEROSIS

(75) Inventors: Raymond V. Damadian, Woodbury, NY (US); Ki-Cheung Chu, Kings Park, NY (US)

(73) Assignee: Fonar Corporation, Melville, NY (US)

( * ) Notice: Subject to any disclaimer, the term of this patent is extended or adjusted under 35 U.S.C. 154(b) by 0 days.

(21) Appl. No.: 13/453,816

(22) Filed: Apr. 23, 2012

Related U.S. Application Data

(60) Provisional application No. 61/478,167, filed on Apr. 22, 2011, provisional application No. 61/532,684, filed on Sep. 9, 2011, provisional application No. 61/614,819, filed on Mar. 23, 2012.

(51) Int. Cl.
| | | |
|---|---|---|
| *A61B 5/05* | (2006.01) | |
| *A61B 5/055* | (2006.01) | |
| *A61B 5/00* | (2006.01) | |

(52) U.S. Cl.
CPC ............ *A61B 5/055* (2013.01); *A61B 5/4836* (2013.01)

(58) Field of Classification Search
CPC ... A61B 5/026; A61B 5/4064; A61B 5/02007; A61B 8/0816
USPC ......... 600/407, 409–411; 324/306–307, 319, 324/321
See application file for complete search history.

(56) References Cited

U.S. PATENT DOCUMENTS

| | | |
|---|---|---|
| 6,677,753 B1 | 1/2004 | Danby et al. |
| 7,123,008 B1 | 10/2006 | Damadian et al. |
| 2003/0059476 A1* | 3/2003 | Wang .......................... 424/523 |
| 2005/0020945 A1* | 1/2005 | Tosaya et al. .................. 601/2 |
| 2006/0051814 A1* | 3/2006 | Jackowski et al. ............ 435/7.1 |
| 2011/0009749 A1* | 1/2011 | Zamboni ...................... 600/454 |

OTHER PUBLICATIONS

Zamboni et al (CSF dynamics and brain volume in multiple sclerosis are associated with extracranial venous flow anomalies: a pilot program), Apr. 2010.*
Hofmann et al (Phase-Contrast MR Imaging of the Cervical CSF and Spinal Cord: Volumetric Motion Analysis in Patients with Chiari I Malformation, AJNR Am J Neuroradial 21:151-158, Jan. 2000).*
Batzdorf et al (Chiari malformation and syringomyelia, 2008).*
Zamboni et al (Intracranial venous haemodynamics in multiple sclerosis, 2007).*
Alperin et al (Quantifying the effect of posture on intracranial physiology in humans by MRI flow studies).*
Damadian et al., "The Possible Role of Cranio-Cervical Trauma and Abnormal CSF Hydrodynamics in the Generis of Multiple Sclerosis", Physiol. Chem. Phys. & Med. NMR (Sep. 20, 2011) 41: 1-17.

* cited by examiner

*Primary Examiner* — Joel F Brutus
(74) *Attorney, Agent, or Firm* — Lerner, David, Littenberg, Krumholz & Mentlik, LLP

(57) ABSTRACT

The present invention relates to a method for monitoring the presence of, or the susceptibility to multiple sclerosis. The method may include obtaining measurements of the cerebrospinal fluid (CSF) flow in a patient using magnetic resonance imaging, and deriving one or more values representing the CSF flow in the patient. These values may be used to determine if the patient has abnormal CSF flow, as such abnormal CSF flow may be indicative of presence of, or susceptibility to multiple sclerosis. The present invention also discloses that magnetic resonance images may be obtained on patients in various positions, including the upright position.

23 Claims, 20 Drawing Sheets

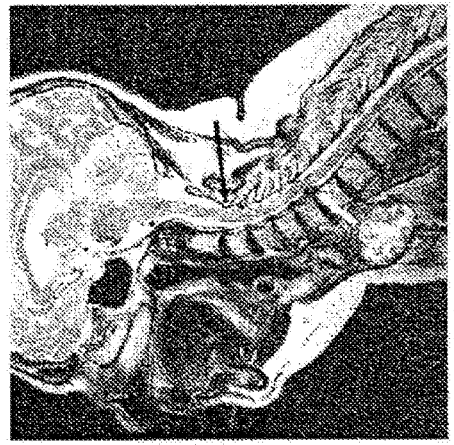
Fig. 1b. Up. T2 Sag C-Spine
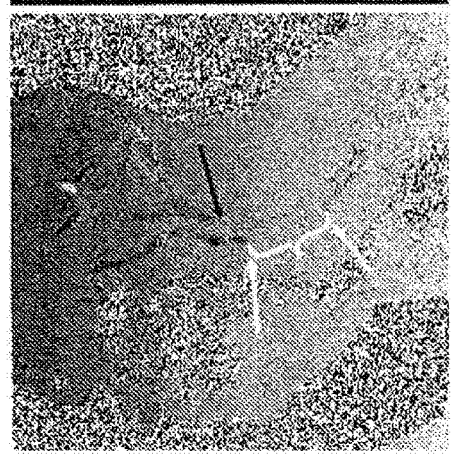
Fig. 1c. Up. Sag CSF
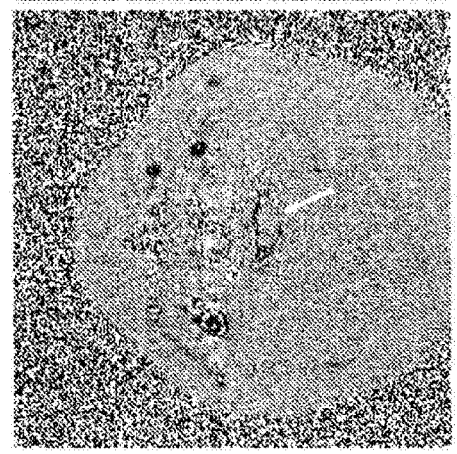
Fig. 1d. Rec. Ax CSF
Fig. 1e. Up. Cr-Cx-Jx Prot.Den Ax.
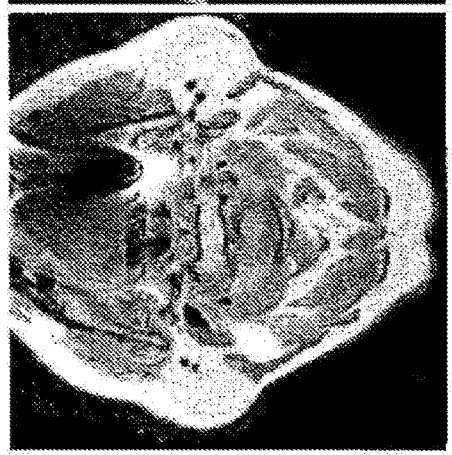
Fig. 1f. Rec. Cr-Cx-Jx Prot.Den Ax.
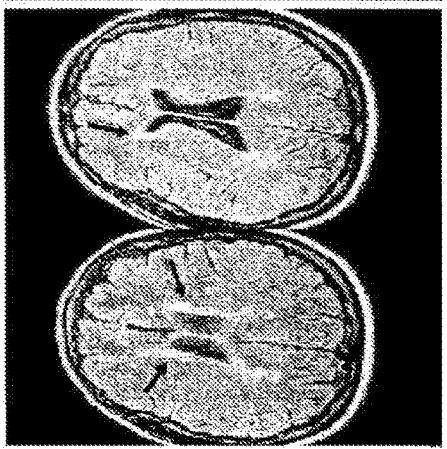
Fig. 1g
Fig. 1h

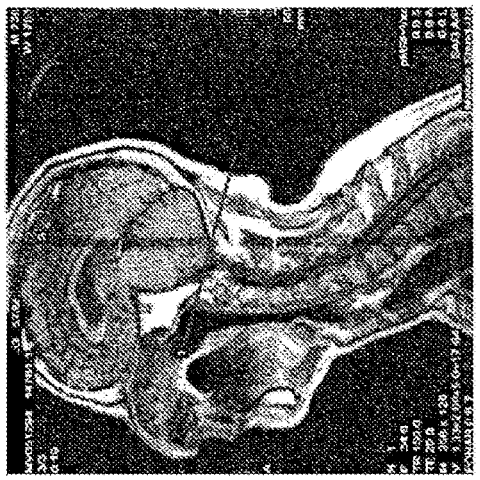
Fig. 2c Scout for 2d
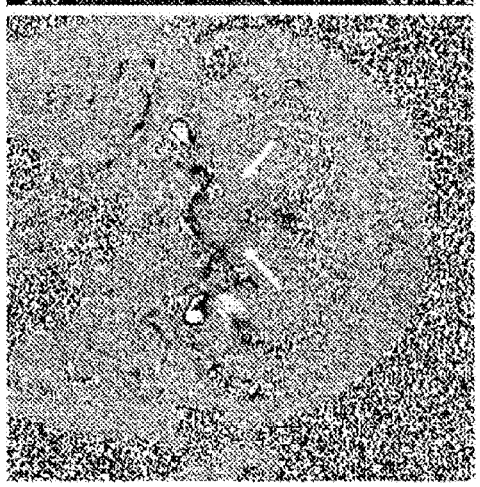
Fig. 2d Up. Ax CSF
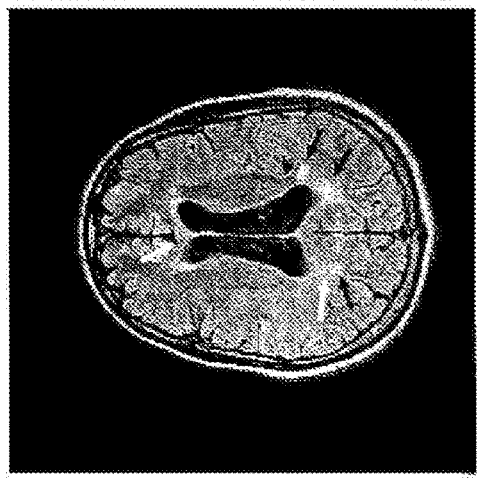
Fig. 2e Up. Ax FLAIR Brn.
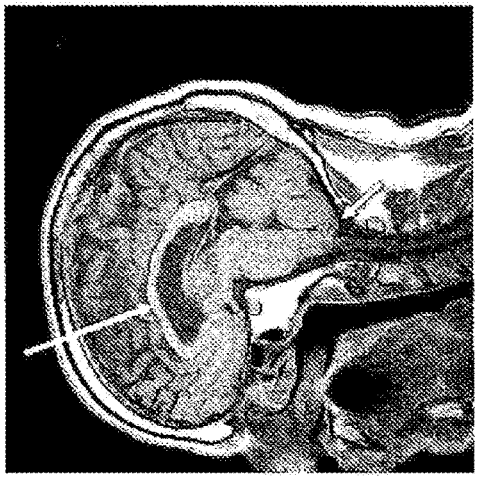
Fig. 2f Up. T1 Sag Brn.
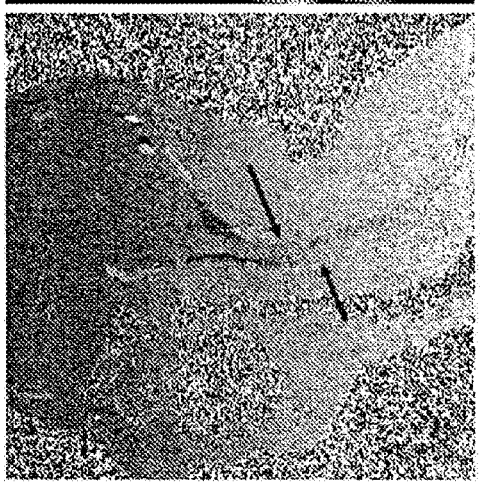
Fig. 2g Up. Sag CSF Flow
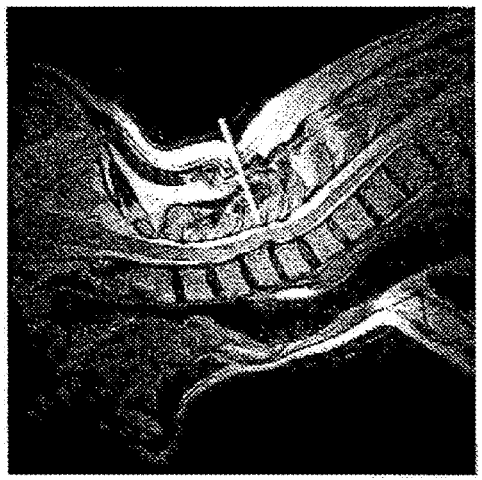
Fig. 2h Up. Sag T2

Fig. 3a. Up. T1 Sag C-Spine
Fig. 3b. Up. Sag CSF
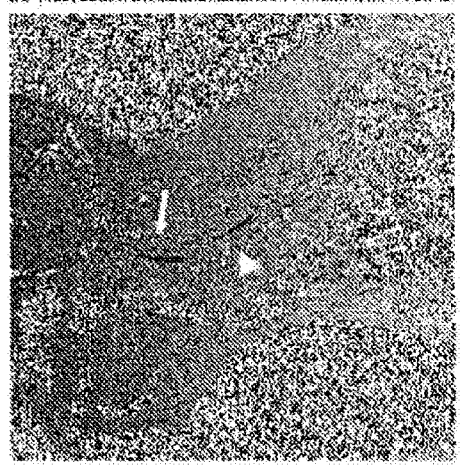
Fig. 3c. Rec. Sag CSF
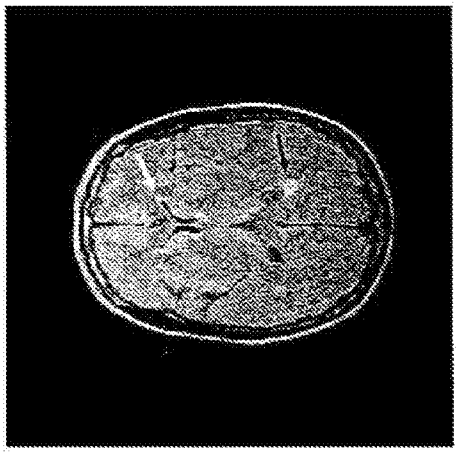
Fig. 3d. Up. Ax FLAIR Brn.
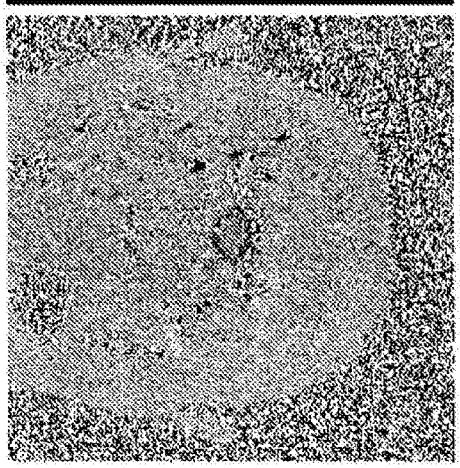
Fig. 3e. Up. Ax CSF Mid C-2
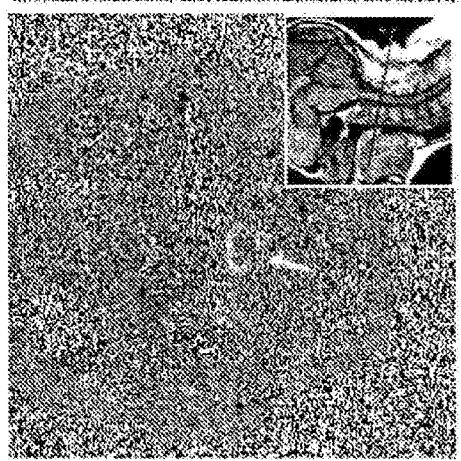
Fig. 3f. Rec. Ax CSF Mid C-2

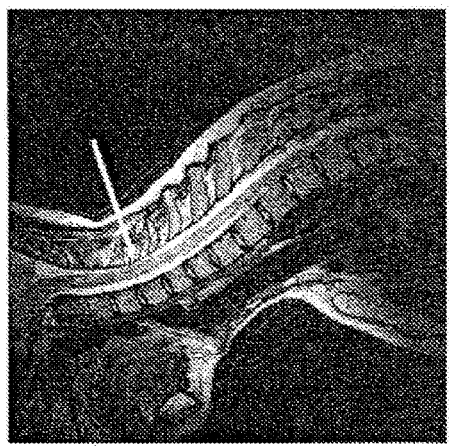
Fig. 4a. Up. Sag T2 Cerv.
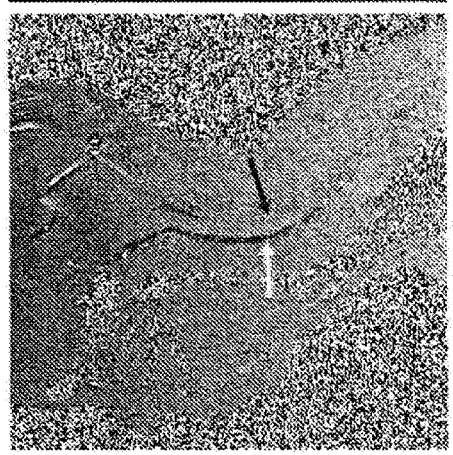
Fig. 4b. Up. Sag CSF Flow
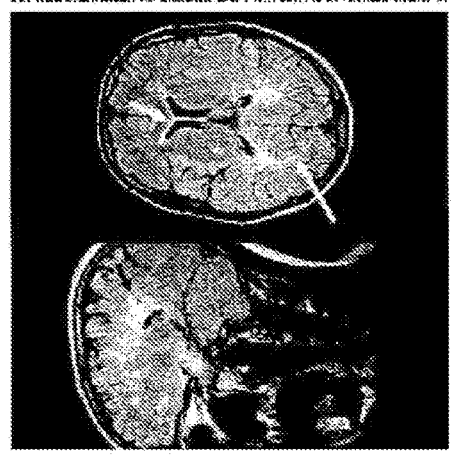
Fig. 4c
Fig. 4d
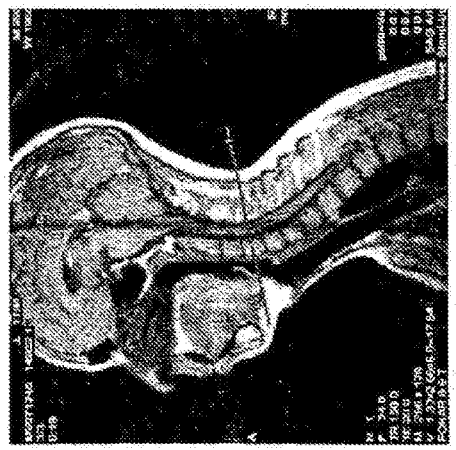
Fig. 4e. Scout for 4f.
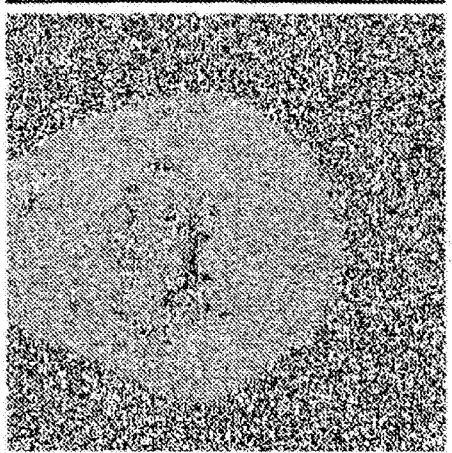
Fig. 4f. Up. Ax CSF Mid C-4
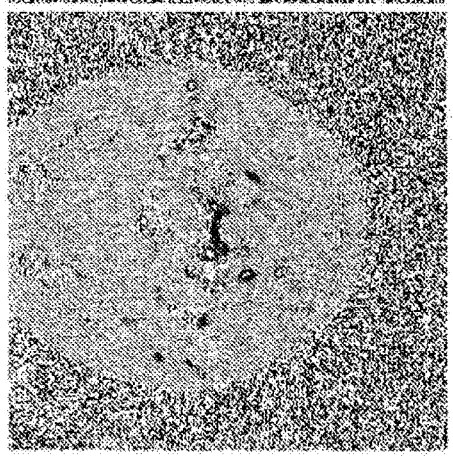
Fig. 4g. Rec. Ax CSF Mid C-3

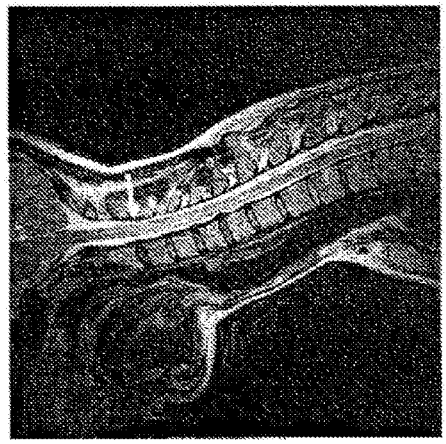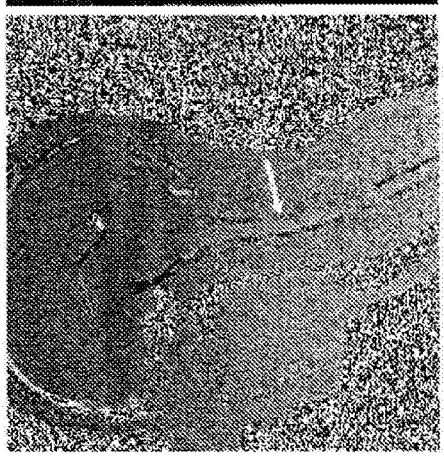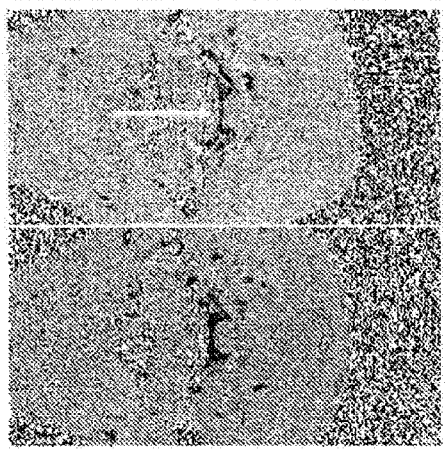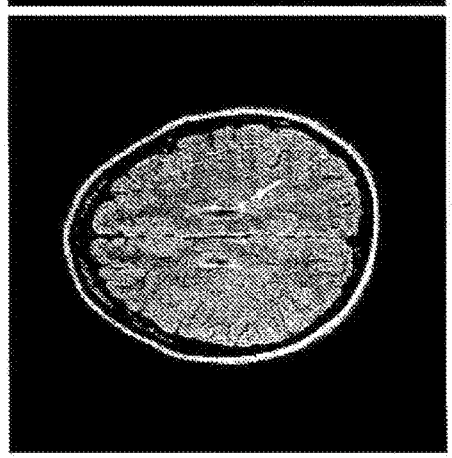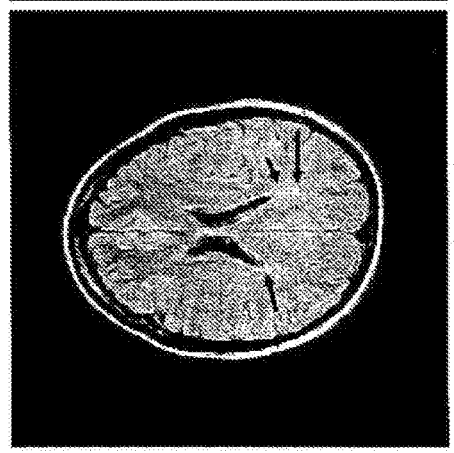
Fig. 5a. Up. T2 Sag C-Spine
Fig. 5b. Up. Sag CSF Flow
Fig. 5c
Fig. 5d
Fig. 5e. Up. Sag FLAIR
Fig. 5f. Up. Ax FLAIR
Fig. 5g. Up. Ax FLAIR

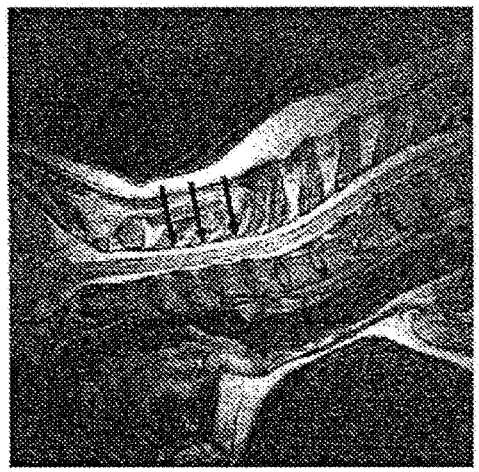
Fig. 6a. Up. T2 Sag C5/6
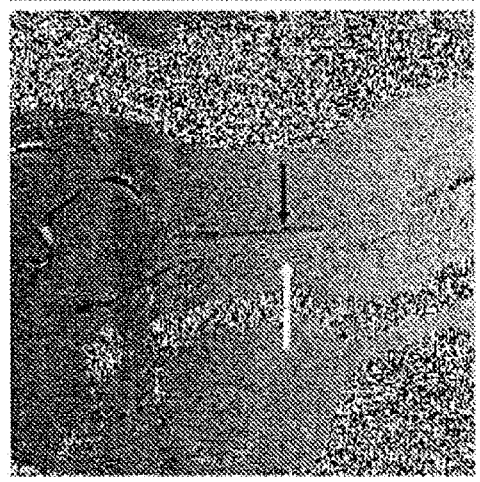
Fig. 6b. Up. Sag CSF Flow
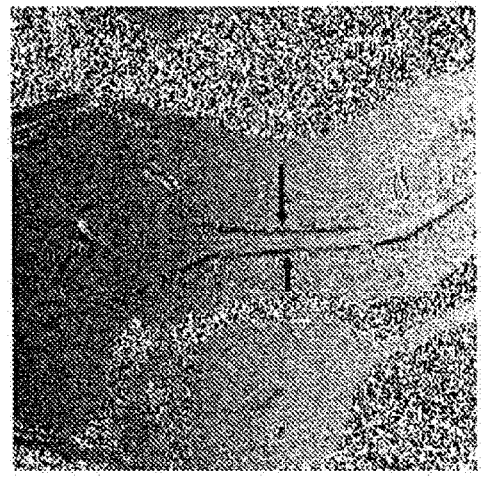
Fig. 6c. Rec. Sag CSF Flow
Fig. 6d. Up. Cer Tonsil Hrn
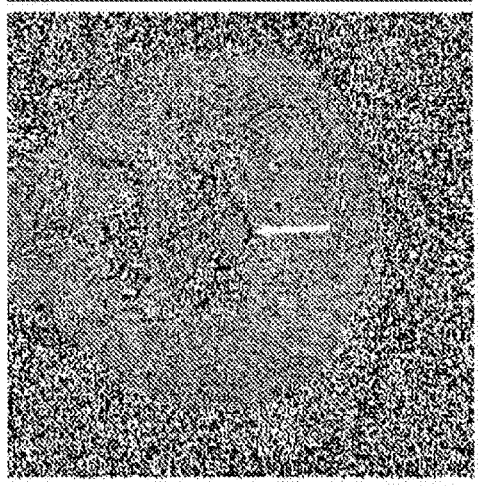
Fig. 6e. Up. Ax CSF Mid C-S
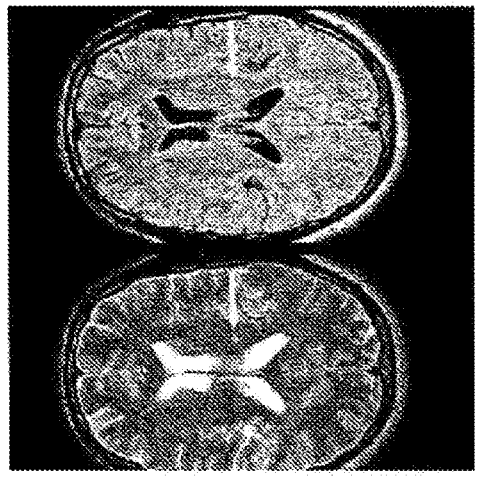
Fig. 6f.
Fig. 6g.

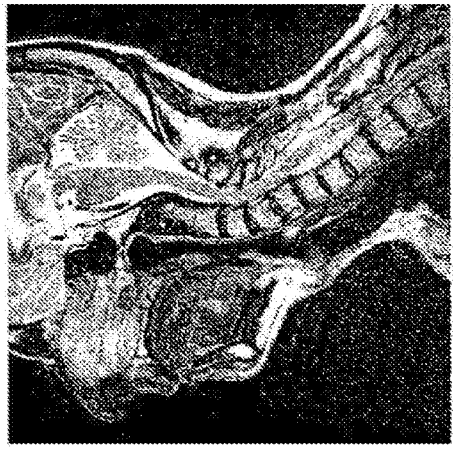
Fig. 7a. Rec. T2 Sag Cerv.
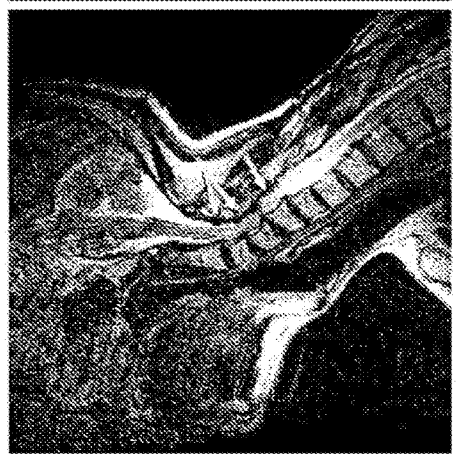
Fig. 7b. Up. T2 Sag Cerv.
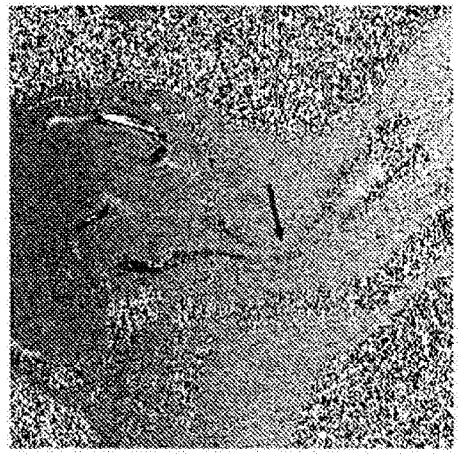
Fig. 7c. Up.Sag CSF Flow
Fig. 7d. Up.Ax FLAIR
Fig. 7e. Up.Ax FLAIR
Fig. 7f. Up.Ax FLAIR

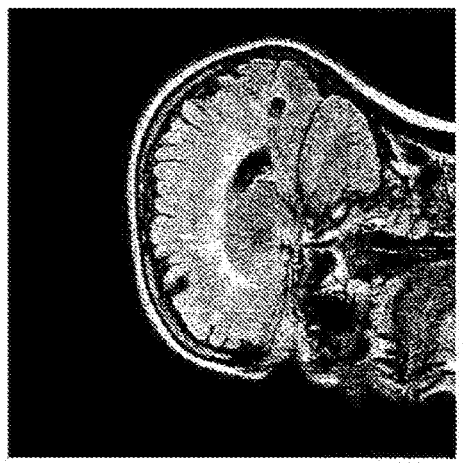
Fig. 8a. Up. Flair Sag Brn.
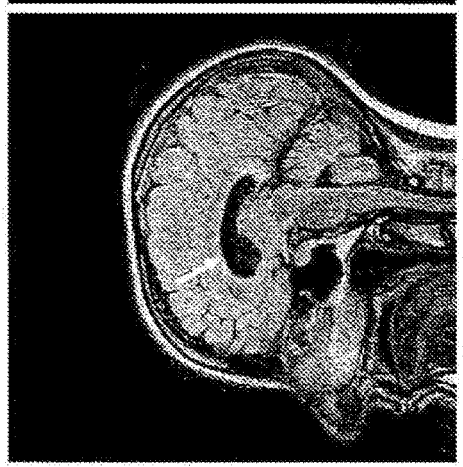
Fig. 8b. Up. Flair Sag Brn.
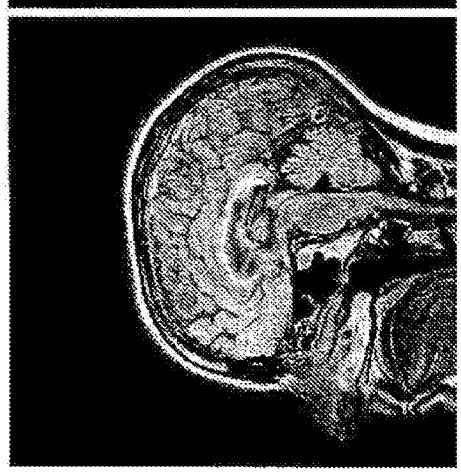
Fig. 8c. Up. Flair Sag Brn.
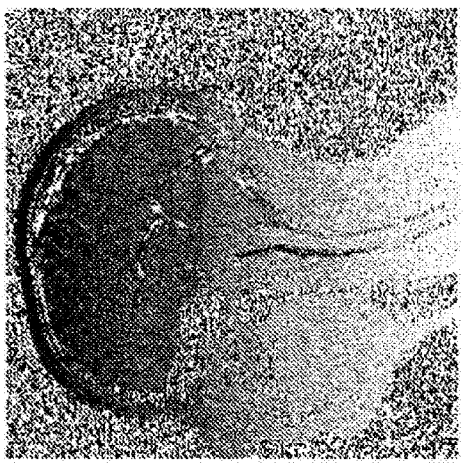
Fig. 8d. Up. Sag CSF Flow
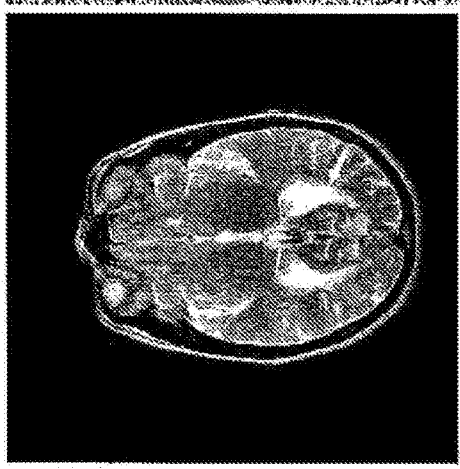
Fig. 8e. Up. T2 Ax Brn.
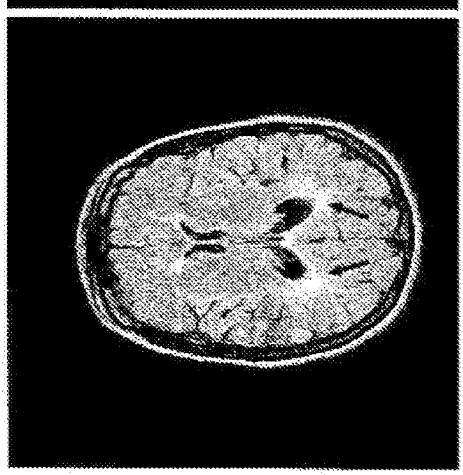
Fig. 8f. Up. Flair Ax Brn.

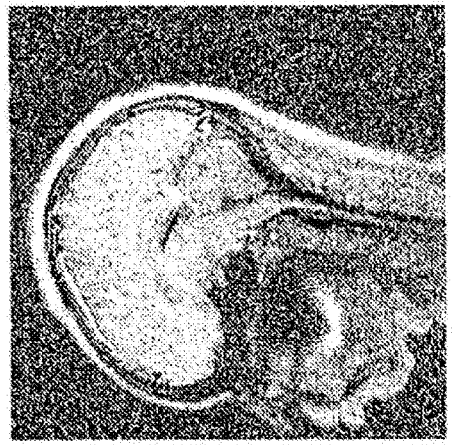
Fig. 9a. Up. Sag CSF Brn.
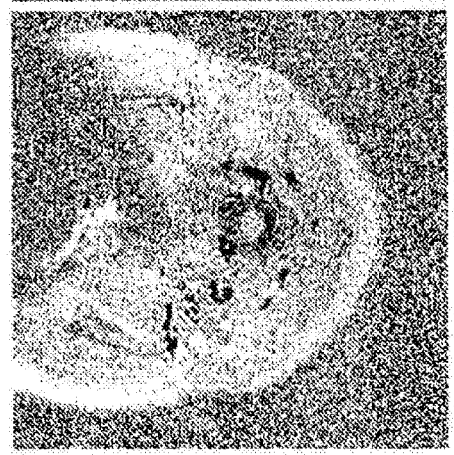
Fig. 9b. Up. Ax CSF Mid C-2.
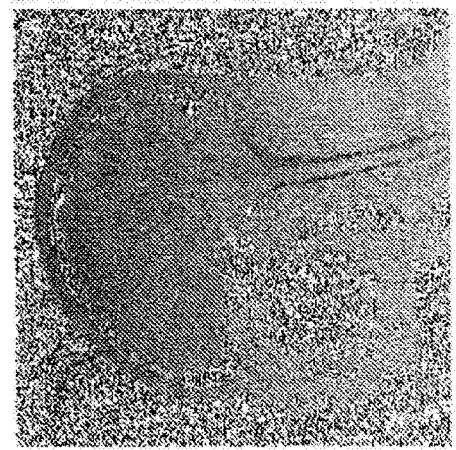
Fig. 9c. Rec. Sag CSF Brn.
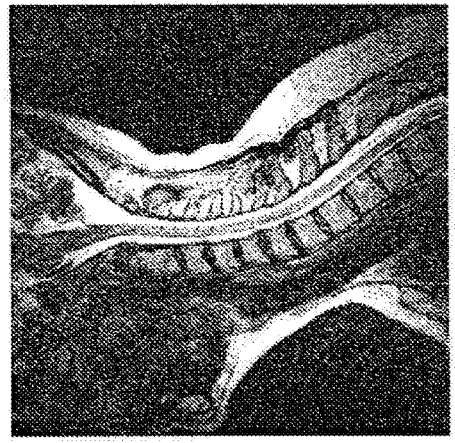
Fig. 10a. Up. T2 Sag C-Spine
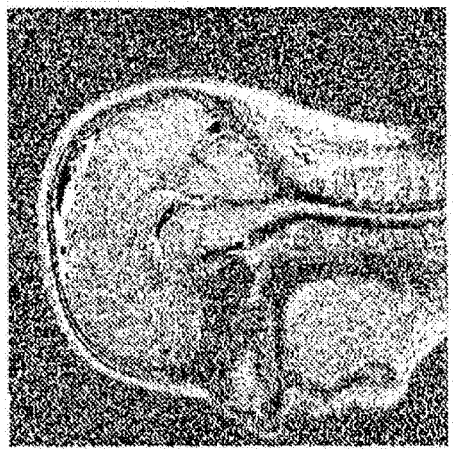
Fig. 10b. Up. Sag CSF Flow
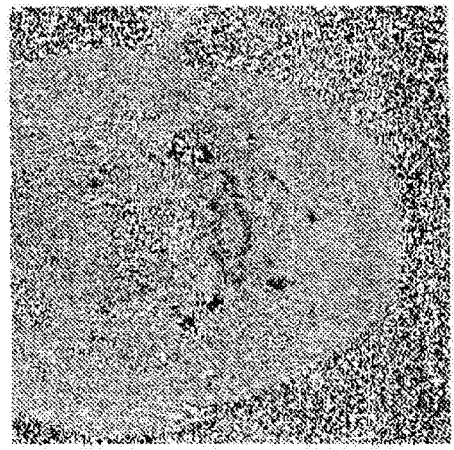
Fig. 10c. Up. Ax CSF Mid C-2

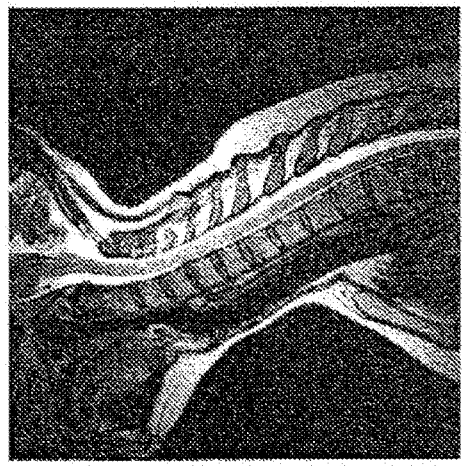
Fig. 11a. Up. T2 Sag C-Spine
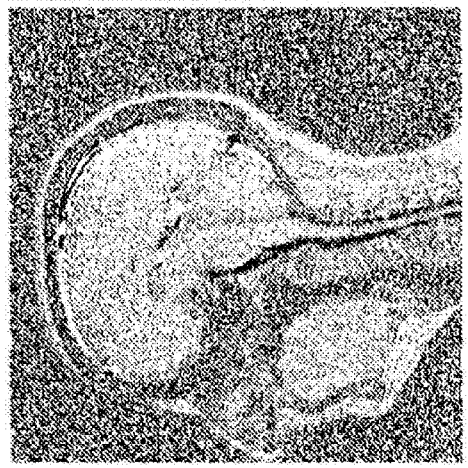
Fig. 11b. Up. Sag CSF Flow
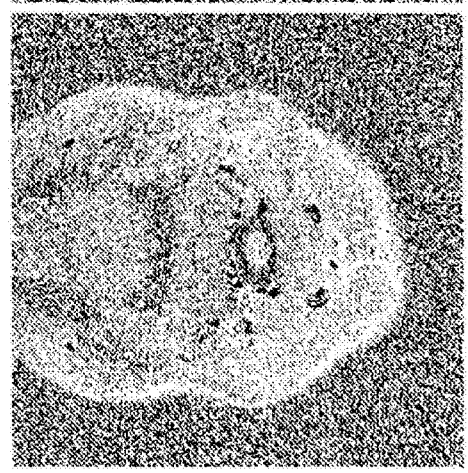
Fig. 11c. Up. Ax CSF Mid C-2
Fig. 12a. Up. T2 Sag C-Spine
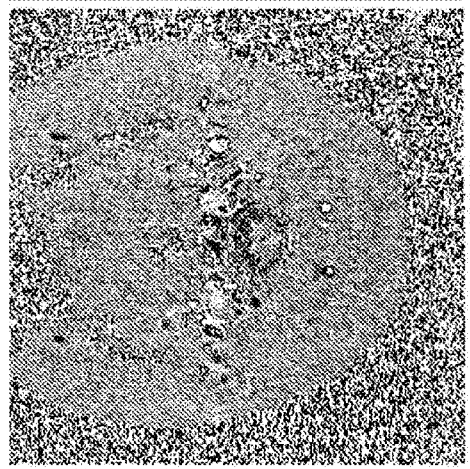
Fig. 12b. Rec. Ax CSF Flow
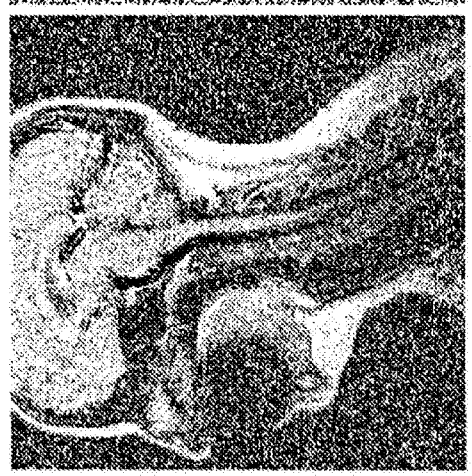
Fig. 12c. Up. Sag CSF Flow

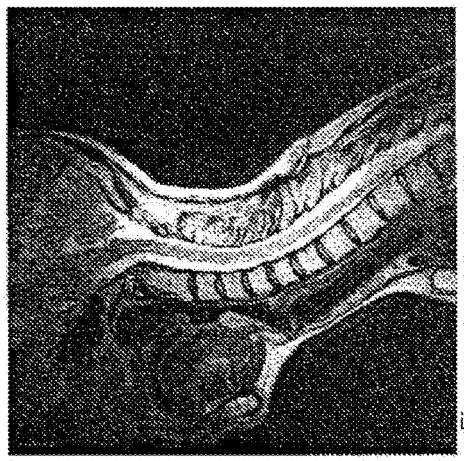
Fig. 13a. Up. T2 Sag C-Spine
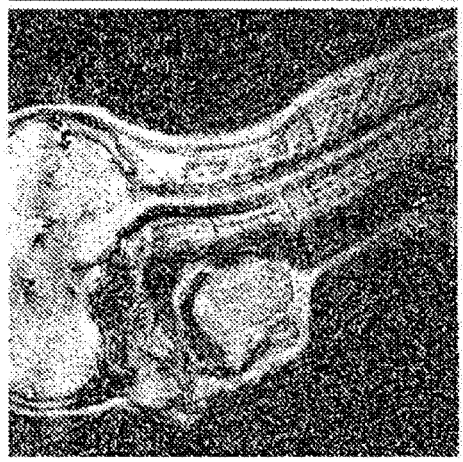
Fig. 13b. Up. Sag CSF Flow
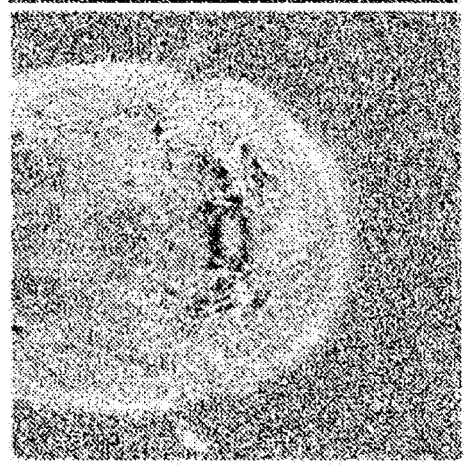
Fig. 13c. Up. Ax CSF Mid C-2
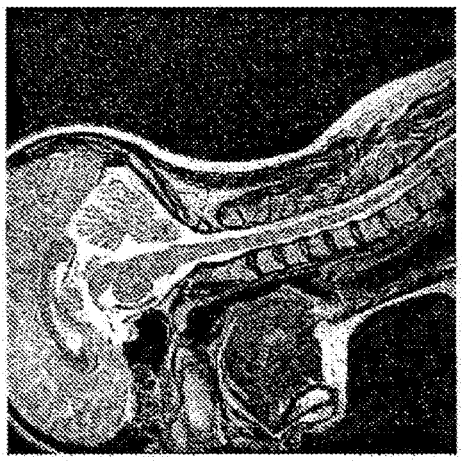
Fig. 14a. Up. T2 Sag C-Spine
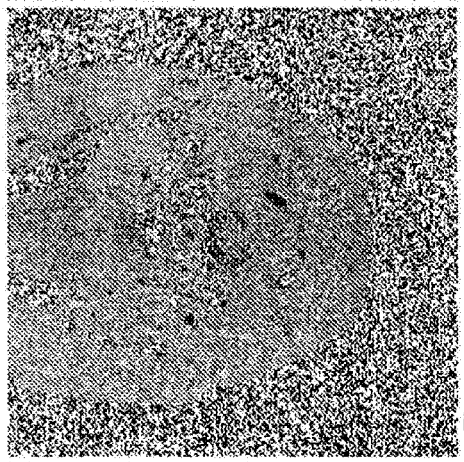
Fig. 14b. Rec. Ax CSF Flow
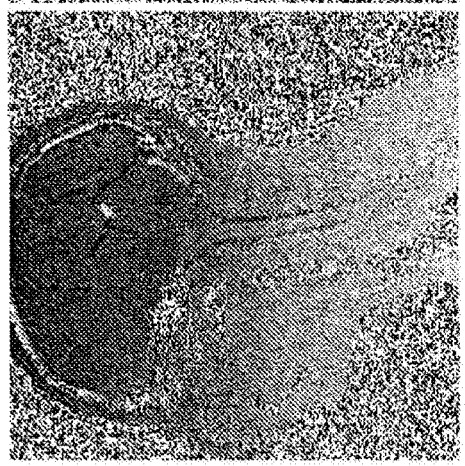
Fig. 14c. Up. Sag CSF Flow

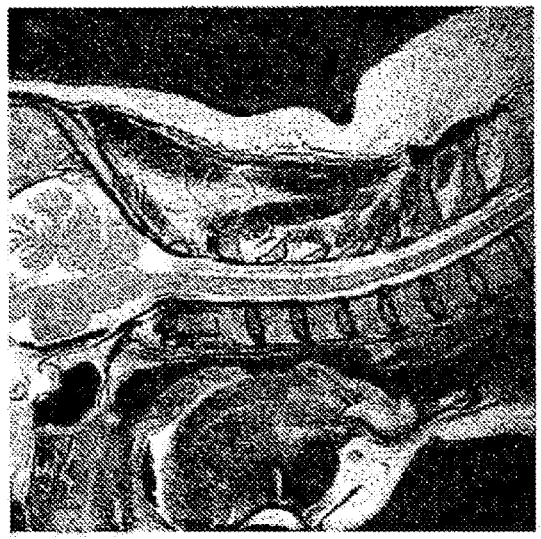
Fig. 15a. Up. T2 Sag C-Spine
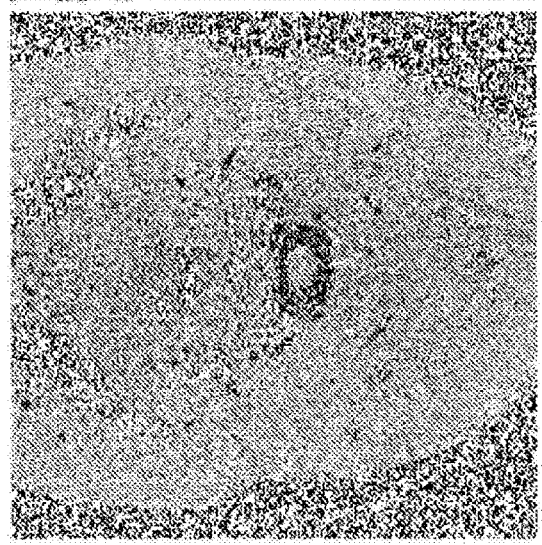
Fig. 15b. Up. Ax CSF Flow
Fig. 15c. Up. Sag CSF Flow Post-treatment Pre-treatment

Fig 17

TABLE 1 - Trauma history and pathological changes in cervical anatomy, CSF hydrodynamics and cinematography in seven MS patients and normals

| Pt. # | History of Serious Prior Cranio-Cervical Trauma | Yrs. Tran. Prec. Dx. | Upright MRI Image Analysis | Recumbent MRI Image Analysis | Up. Peak Sys. CSF Vel. (out-flow) cm/sec | Rec. Peak Sys. CSF Vel. (out-flow) cm/sec | Up. Peak Dias. CSF Vel. (in-flow) cm/sec | Rec. Peak Dias. CSF Vel. (in-flow) cm/sec | Up. Press. Grad. Peak to Peak mmHg/cm | Rec. Press. Grad. Peak to Peak mmHg/cm | Up. MRI CSFfl Ciné | Rec. MRI CSFfl Ciné | Pt. # |
|---|---|---|---|---|---|---|---|---|---|---|---|---|---|
| | | | ← see glossary → | ← glossary → | | | | | | | ← see glossary → | | |
| 1 | MVA Whip.- rear impact collison by a pickup truck while stopped at a traffic light | 8 | 1)C2 c.clock rot. 16°, 2)C6/7 cd.c., c.sten. | 1)C2 c.clock rot. 5.7°, 2)po c.strn., no cd.c. | .67 | 1.52 | .40 | .745 | .012 | .024 | 1)dors. CSFfl. obst. at C2/3, 2)vent. CSFfl. obst. C3 to C5/6, 3)vent. CSFfl. not obst. by C6/7 disc. hm. when Up. | 1)dors. CSFfl. faint but infra, 2)vent. CSFfl. infra. to C6/7, 3)vent. CSFfl. obst. at C6/7 by disc. hm. | 1 |
| 2 | cranio-cervical trauma - 20 ft. ladder collapse | 2 | 1)r.lis. C5, 2)cd.c., c.sten. C5/6, 3)Higfl. cd.c. C6/7, ligfl. can. obst. C6/7, 4)c.sten. C6/7 | 1)vent. can.obs, 2)r.lis., c.sten. red, 3)Higfl. obst. absent | 2.58 | 1.39 | 1.047 | 1.033 | .054 | .031 | 1)dors. CSFfl. obst top C2 to C3/4, 2)dors. CSFfl. obst C5/6, 3)vent. CSFfl. obst. bel. C3/4 | 1)vent. CSFfl. obst. C3/4 & bel. | 2 |
| 3 | MVA Whip.- rear impact collison by a pickup truck; car trunk compressed to rear window; neck pain back of neck | 21 | 1)r.lis C4, C5, 2)cd.c., c.sten. C4/5, 3)Higfl. cd.c. C4/5, 4)sp.cd. abut. C5/6 5)hm. dsc. C2/3, C3/4, C4/5, C5/6, C6/7 | 1)r.lis. red, 2)po sp.cd abut. C5/6 | 1.14 | .336 | .394 | .702 | .016 | .011 | 1)vent. CSFfl. obst. & bel., 2)dors. CSFfl. obst C2/3 to C5/6, 3)C.sten C2/3, C4/5, 4)higfl. obst. CSFfl. C2/3, C4/5, C5/6 | 1)vent. & dors. CSFfl. infra. | 3 |
| 4 | cervical trau. age 6, daily violent parental shoulder shaking | 9 | 1)sp.cd. P., 2)C3/4 dors. can.obs., 3)CTB 2mm | 1)sp.cd. more A., 2)dent. can. pat., 3)CTB 1mm | 1.80 | 2.71 | .464 | 1.36 | .036 | .063 | 1)dors. CSFfl. obst. bel. C2/3, 2)vent. CSFfl. infra. | 1)dors. CSFfl. obst. bel. C2/3, 2)vent. CSFfl. infra. | 4 |
| 5 | ballerina, 4 ½ hours daily practice ages 12-17 | 9 | 1)c.sten. hrn. at C3/4, C4/5, C5/6, 2)disc. bulges at C2/3, C6/7 | 1)C2/3, C5/6 disc. hm. 2)C3/4 hm. absent 3)C4/5 less disc. bulge 4)C6/7 disc. bulge not present | 2.03 | 2.14 | .731 | 1.55 | .050 | .046 | 1)dors. CSFfl. obst. C2/3 to C5, 2)vent. CSFfl. obst. at C2/3, C3/4, C4/5, C5/6 | 1)vent. CSFfl. int. less when pt. Rec. | 5 |
| 6 | MVA Whip.- age 19 hit post in parking lot; head went forward and back; lt. clavical fractured; could not move neck; unable to move lt. arm; neck collar worn for 2 weeks following accident | 11 | 1)CTB 3mm | 1)CTB 2mm | .79 | .94 | .32 | .80 | .012 | .020 | 1)vent. CSF fl. obst. C2/3 to C6 | 2)no CSFfl. int. when pt. Rec. | 6 |
| 7 | MVA - neck injury; seat belt came across lt. neck; spasms in both legs, neck surgery for spondy. 2 years post MVA | 1 | 1)vent. cd. c. C2 to C6, 2)r.lis. C5, 3)higfl. can.obs. C2/3 | 1)cd.c. red. C2 to C6, 2)C5 r.lis. red. | .865 | - | .51 | - | .024 | - | 1)dors. CSFfl. obst C2/3 to C4/5, 2)vent. CSFfl. obst. at C5 | 1)dors. CSFfl. obst. C2/3 & bel. | 7 |
| | Mean Value (7 patients) | | | | 1.41 | 1.51 | .552 | 1.03 | | | | | |
| 8 | normal volunteer | | | | .571 | .950 | .256 | 1.06 | .0143 | .029 | CSFfl. inta. vent. & dors. | CSFfl. inta. vent. & dors. | 8 |
| 9 | normal volunteer | | | | 1.07 | .751 | .414 | .457 | .0206 | .017 | CSFfl. inta. vent. & dors. | CSFfl. inta. vent. & dors. | 9 |
| 10 | normal volunteer | | | | .613 | 1.03 | .352 | .825 | .0115 | .0232 | CSFfl. inta. vent. & dors. | CSFfl. inta. vent. & dors. | 10 |
| 11 | normal volunteer | | | | .839 | 1.09 | .392 | .827 | .0073 | .019 | CSFfl. inta. vent. & dors. | CSFfl. inta. vent. & dors. | 11 |
| 12 | normal volunteer | | | | .752 | 1.05 | .322 | .746 | .0181 | .023 | CSFfl. inta. vent. & dors. | CSFfl. inta. vent. & dors. | 12 |
| | Mean Value (normals) | | | | .769 | .974 | .343 | .783 | .0145 | .022 | | | |
| | | | | | +/-.20 | +/-.135 | +/-.062 | +/-.217 | +/-.0053 | +/-.0046 | | | | a-A.,anterior; abut.,abutment; b-bel.,below; c-c.sten.,spinal canal stenosis; can.,canal; can.obs.,spinal canal obstruction; c.clock,counter clockwise; cd.,cord; cd.c.,cord compression; Cran.,cranial; CSFfl.,CSF flow; CTB,cerebellar tonsil ectopia; d-dias.,diastolic; dors.,dorsal; dsc.,disc; Dx.,diagnosis; F-Grad.,gradient; h- hrn.,herniation; i-int.,interruption; inta.,intact; Higfl.,ligamentum flavum; l-left; m-MVA.,motor vehicle accident; o-obst.,obstructed,obstruction; p-P.,posterior; pat.,patient; Pres.,pressure; r-Rec.,Recumbent; red.,reduced; r.lis.,retrolisthesis; rot.,rotation; rt.,right; s- sp.cd.,spinal cord; sys.,systolic; t-trau.,trauma; u-Up.,Upright; v-vent.,ventral; w-Whip.,Whiplash; y-yrs.,years       BOLDED numbers Col. 5-10 (P<.05); Italicized numbers Col. 5-10 (P<.053 - <.07) (1/11/10)

Fig 18

TABLE 2A. Anatomic Images, CSF Flow Images and CSF Flow Quantification of MS Patients

| 1 | 2 | 3 | 4 | 5 | 6 | 7 | 8 | 9 | 10 | 11 | 12 | 13 |
|---|---|---|---|---|---|---|---|---|---|---|---|---|
| Patient # | Up. Peak Sys CSF Vel. (outflow) cm/sec | Rec. Peak Sys. CSF Vel. (outflow) cm/sec | Up. Peak Diss. CSF Vel. (inflow) cm/sec | Rec. Peak Dias. CSF Vel. (inflow) cm/sec | Up. Press. Grad. Peak to Peak mmHg/cm | Rec. Press. Grad. Peak to Peak mmHg/cm | Upright MRI Image Analysis ——see glossary—— | Recumbent MRI Image Analysis | UPRIGHT MRI Ciné CSF Flow Analysis ——see glossary—— | Recumbent MRI Ciné CSF Flow Analysis | MRI Image Differences Up./Rec. | CSF Ciné Differences Up./Rec. |
| Patien #1 (MVA #1) | .67 | 1.52 | .40 | .745 | .012 | .024 | 1)C2 c.clock rot.16°, 2)C6/7 cd.c., c.sten. | 1)C2 c.clock rot.5.7° 2)no c.sten., no cd.c. | 1)dors. CSFfl. obst. at C2/3 2)vent. CSFfl. obst. C3 to C5/6, 3)vent. CSFfl. not obst. by C/67 dsc. hrn. when Up. | 1)dors. CSFfl. faint but intal, 2)vent. CSFfl. inta. to C6/7, 3)vent. CSFfl. obst. at C6/7 by disc. hrn. | 1)C2 rotated 16° Up., 5.7° REc. | 1)vent. CSFfl. obst. Up. but not Rec. | 1 |
| Patient #2 | 2.58 P<.05 | 1.39 P<.05 | 1.047 P<.05 | 1.033 | .054 P<.05 | .031 | 1)r.lis. C5, 2)cd.c. c.sten. C5/6 3)ligfl. cd.c. C6/7, ligfl. can. obst. C6/7 4)c.sten. C6/7 | 1)vent. can.obs., 2)r.lis. c.sten. red. 3)ligfl. obst. absent | 1)dors. CSFfl. obst. top C2 to C3/4, 2)dors. CSFfl. obst. C5/6, 3)vent. CSFfl. obst. bel. C3/4 | 1)vent. CSFfl. obst. C3/4 & bel. | 1)no infolding ligfl. Rec., 2)less c.sten. Rec. | 1)CSFfl. obst Up., 2)full circumspinal CSFfl. Rec. | 2 |
| Patient #3 (MVA #2) | 1.14 | .336 | .394 | .702 | .016 | .011 | 1)r.lis. C4, C5, 2)cd.c, c.sten. C4/5, | 1)r.lis. red., 2)no sp.cd. abut. C5/6 | 1)dors. CSFfl. obst. C2/3 to C5/6, 2)vent. CSFfl. obst. C2/3 | 1)vent. & dors. CSFfl. inta. | 1)C4, C5 listhesis, much less Rec. | 1)CSFfl. obst. Up., 2)CSFfl. unobst. Rec. | 3 |
| Patient #4 | 1.80 P<.05 | 2.71 P<.05 | .464 | 1.36 P<.05 | .036 P<.05 | .063 | 1)sp.cd. post. 2)C3/4 dors. can.obs., 3)CTE 2mm 4)sp.cd. abut. post. wall sp.can. C3/4 | 1)sp.cd. more ant., 2)dors. can. pat., 3)CTE 1mm | 1)dors. CSFfl. obst. bel. C2/3, 2)vent. CSFfl. inta. | 1)dors. CSFfl. obst. bel. C2/3, 2)vent. CSFfl. inta. | 1)cord more ant. Rec. | 1)same CSFfl. obst. Up. & Rec. | 4 |
| Patient #5 | 2.03 P<.05 | 2.14 P<.05 | .731 P<.05 | 1.55 P<.05 | .050 P<.05 | .046 P<.05 | 1)dsc. hrn. at C3/4, C4/5, C5/6 2)dsc. bulges at C2/3, C6/7 | 1)C2/3, C5/6 dsc. hrn. 2)C3/4 hrn. absent 3)C4/5less dsc. bulge 4)C6/7 dsc. bulge not present | 1)dors. CSFfl. obst. C2/3 to C5, 2)vent. CSFfl. obst. at C2/3, C3/4, C4/5, C5/6 | 1)vent. CSFfl. int. less when patient Rec. | 1)C5/6 hrn. less Rec. | 1)vent. CSFfl. less inter. Rec. | 5 |

Fig. 18 (continued)

| 1 | 2 | 3 | 4 | 5 | 6 | 7 | 8 | 9 | 10 | 11 | 12 | 13 | |
|---|---|---|---|---|---|---|---|---|---|---|---|---|---|
| Patient # | Up. Peak Sys CSF Vel. (outflow) cm/sec | Rec. Peak Sys. CSF Vel. (outflow) cm/sec | Up. Peak Diss. CSF Vel. (inflow) cm/sec) | Rec. Peak Dias. CSF Vel. (inflow) cm/sec | Up. Press. Grad. Peak to Peak mmHg/cm | Rec. Press. Grad. Peak to Peak mmHg/cm | Upright MRK Image Analysis | Recumbent MRI Image Analysis | UPRIGHT MRI Ciné CSF Flow Analysis | Recumbent MRI Ciné CSF Flow Analysis | MRI Image Differences Up./Rec. | CSF Ciné Differences Up./Rec. | |
| Patent #6 | .79 | .95 | .32 | .80 | .014 | .020 | 1)CTE 2mm | 1)CTE 2mm | 1)vent. CSFfl. obst. C2/3 to C6 | 1)no CSFfl. int. when patient Rec. | 1)no difference | 1)vent. CSFfl. obst. C2/3 to C6 Up. 2)no CSFfl. inter. Rec. | 6 |
| Patient #7 | .865 | --- | .51 | --- | .024 | --- | 1)cd.c. C2/3 to C5/6 2)r.lis C5 | 1)cd. c. red. C2 to C6 2)C5 r.lis. red. (2003 conventional recumbent MRI) | 1)dors. CSFfl. obst. C2/3 to C4/5, 2)vent. CSFfl. obst. at C5 | 1)dors. CSFfl. obst. C2/3 & bel. (2003 conventional recumbent MRI) | 1)less cd.c. C2 to C6, 2)r. lis. red. Rec. | 1)CSFfl. obst. at C2/3 but resotred at C4/5 Up. 2)not restored bel. C4/5 Rec. (2003 conventional recumbent) | 7 |
| Patient #8 (MVA #5) | .818 | --- | .380 | --- | .020 | --- | 1)post. disp. sp. cd. at C2/3, obst. dors. CSFfl. at C2/3 2)markedly enlarged occipital horns 1at. ventcls. 3)peri-ventcl. ed. occipital horns 4)CTE - T2 axials 5)rot. C3 c. wise | 1)dors. CSFfl. obst. C2/3 | | | | | 8 |
| Mean Value (MS patients) | 1.34 (8 pat.) | 1.51 (6 pat.) | .531 (8 pat.) | 1.03 (6 pat.) | .028 (8 pat.) | .033 (6 pat.) | | | | | | | | a-ant., anterior; abut, abutment; b-bel, below; c-c.clock, counter clockwise; c.stern., spinal cnal stenosis; c.wise, clockwise; can., canal; can.obiss., spinal dors., dorsal; dsc, disc; e-ed., edema; g-grad., gradient; h-hrn., herniation; i-inter, interruption; inta., intact; l-lat., lateral; ligfl., ligamentum flavum; red., reduced; rot., rotation; s-sp., spinal; sp.cd., spinal cord; sys., systolic; u-unobst., unobstructed; Up., upright; v-vel., velocity; vent., ventral; -- BOLDED numbers Col.2-7 (P<.05); canal obstruction; cd.c., cord compression; cent., central; CSFfl, CSF flow; CTE, cerebellar tonsil ectopia; d-dias, diastolic; disp., displaced; m-MVA, motor vehicle accident; o-obst. obstructed, obstruction; p-pat., patent; post., posterior, press., pressure; r-r. lis., retrolisthesis; Rec., recumbent; ventcls., ventricles

Fig 19

TABLE 2B. Anatomic Images, CSF Flow Images and CSF Flow Quantification of Normal Examinees

| 1 | 2 | 3 | 4 | 5 | 6 | 7 | 8 | 9 | 10 | 11 | 12 | 13 |
|---|---|---|---|---|---|---|---|---|---|---|---|---|
| Patient # | Up. Peak Sys CSF Vel. (outflow) cm/sec | Rec. Peak Sys. CSF Vel. (outflow) cm/sec | Up. Peak Dias. CSF Vel. (inflow cm/sec) | Rec. Peak Dias. CSF Vel. (inflow) cm/sec | Up. Press. Grad. Peak to Peak mmHg/cm | Rec. Press. Grad. Peak to Peak mmHg/cm | Upright MRK Image Analysis | Recumbent MRI Image Analysis | UPRIGHT MRI Ciné CSF Flow Analysis | Recumbent MRI Ciné CSF Flow Analysis | MRI Image Differences Up./Rec. | CSF Ciné Differences Up./Rec. |
| Normal #1 | 1.07 | .751 | .414 | .457 | .021 | .017 | | | CSFfl. inta. vent & dors. | CSFfl. inta. vent & dors. | | |
| Normal #2 | .613 | 1.03 | .332 | .825 | .0114 | .023 | | | CSFfl. inta. vent & dors. | CSFfl. inta. vent & dors. | | |
| Normal #3 | .752 | 1.05 | .321 | .746 | .0181 | .023 | | | CSFfl. inta. vent & dors. | CSFfl. inta. vent & dors. | | |
| Normal #4 | .640 | .976 | .301 | .626 | .0135 | .0135 | | | CSFfl. inta. vent & dors. | CSFfl. inta. vent & dors. | | |
| Normal #5 | 1.27 | .595 | .526 | .488 | .0227 | .0126 | | | CSFfl. inta. vent & dors. | CSFfl. inta. vent & dors. | | |
| Normal #6 | .586 | .849 | .325 | .786 | .018 | .016 | | | CSFfl. inta. vent & dors. | CSFfl. inta. vent & dors. | | |
| Normal #7 | 1.32 | 1.022 | .583 | 1.08 | .020 | .019 | | | CSFfl. inta. vent & dors. | CSFfl. inta. vent & dors. | | |
| Mean Value (normal examinees)(n=7) | .893 | .896 | .4004 | .715 | .0177 | .108 | | | | | | |
| +/- | .319 | .172 | .1124 | .215 | .0040 | .004 | | | | | | | a-ant., anterior; abut, abutment; b-bel, below; c-c.clock, counter clockwise; c.wise, clockwise; can., canal; can.obis., spinal cnal stenosis; c.stern., cisterna; dors., dorsal; dsc., disc; e-ed., edema; g-grad., gradient; h-hrn., herniation; i-inter., interruption; inta., intact; l-lat., lateral; ligfl., ligamentum flavum; red., reduced; rot., rotation; s-sp., spinal; sp.cd., spinal cord; sys., systolic; u-unobst., unobstructed; Up., upright; v-vel., velocity; vent., ventral; canal obstruction; cd.c., cord compression; cent., central; CSFfl., CSF flow; CTE, cerebellar tonsil ectopia; d-dias., diastolic; disp., displaced; m-MVA, motor vehicle accident; o-obst. obstructed, obstruction; p-pat., patent; post., posterior; press, pressure; r-r.lis., retrolisthesis; Rec., recumbent; ventcls., ventricles

MONITORING AND TREATMENT OF MULTIPLE SCLEROSIS

The present application claims the benefit of the filing date of U.S. Provisional Patent Application No. 61/478,167 filed Apr. 22, 2011, 61/532,684 filed Sep. 9, 2011, and 61/614,819 filed Mar. 23, 2012, the disclosures of which are hereby incorporated herein by reference.

BACKGROUND OF THE INVENTION

Multiple Sclerosis (MS) is a debilitating disease. Although considerable effort has been devoted to diagnosis and treatment of MS, still further improvement would be desirable.

SUMMARY OF THE INVENTION

One aspect of the invention incorporates the realism that Multiple Sclerosis may be biomechanical in origin wherein traumatic injuries to the cervical spine result in cervical pathologies that impede the normal circulation of CSF to and from the brain. The resulting obstruction of CSF outflow from the brain may impair the outflow of CSF from the lateral ventricles of the brain where 500 cc of cerebrospinal fluid is generated daily by the choroid plexuses (20). The obstruction to CSF outflow may result in an increase in ventricular CSF pressure (ICP) which in turn could result in "leakage" of cerebrospinal fluid and its content of more than 300 polypeptides and at least six (6) antigenic proteins (e.g., tau proteins) into surrounding brain parenchyma. The attachment of antigenic proteins to surrounding brain nerve fibers could stimulate the antigen-antibody reactions that produce the axon demyelinations characteristic of MS.

Thus, as described in greater detail in Exhibit A, one aspect of the present invention incorporates the realization that impeded or accelerated cerebrospinal fluid ("CSF") flow, hereinafter referred to as "abnormal" CSF flow, is associated with the presence of multiple sclerosis ("MS"). Although the present invention is not limited by any theory of operation, it is believed that anatomical abnormalities such as abnormalities of the cranial anatomy or of the cervical anatomy which can impede CSF flow are associated with the presence of MS and with a greater probability of future development of MS. Stated another way, if a patient currently does not exhibit conventional symptoms of MS, but has significant obstruction to CSF flow from the ventricles of the brain to the subarachnoid space or from the subarachnoid space to the ventricles, the patient will have an increased risk of developing MS in the future. It is believed that this association arises from the role played by CSF leakage into the brain parenchyma and antigen-antibody responses of the brain tissues to the CSF leaks. Regardless of the mechanism of operation, impeded CSF flow and the presence of anatomical abnormalities which can impede CSF flow, are indicative of presence or increased risk of developing MS.

As set forth in greater detail in the Examples below, a method for monitoring for presence of or susceptibility to MS in accordance with one aspect of the present invention desirably includes measuring CSF flow in a patient using magnetic resonance imaging ("MRI") to derive one or more values representing the CSF flow in the patient. The method desirably further includes the step of determining if the one or more values derived in the measuring step demonstrate abnormal CSF flow. The presence of one or more values demonstrating abnormal CSF flow is indicative of the presence of or enhanced susceptibility to MS. The determining step may include comparing the one or more values derived in the measuring step to a standard.

A further aspect of the present invention provides a method of medical treatment which includes examining a patient having known or suspected MS to detect anatomical abnormalities capable of significantly altering cerebrospinal fluid flow. For example, the abnormalities may significantly impede CSF flow. In another example, the abnormalities may accelerate CSF flow. Desirably, the method according to this aspect of the invention further includes the step of treating the patient to reduce intracranial CSF pressure responsive at least in part to detection of one or more of said abnormalities. The method may further include measuring CSF flow, and treatment may be performed responsive to detection of impeded CSF flow alone or in combination with the anatomical abnormalities. The treatment may include, for example, surgical repair of the anatomical abnormalities, or other treatments which have the effect of reducing intracranial CSF pressure. This aspect of the invention incorporates the realization that in a patient having MS, anatomical abnormalities related to CSF flow, impeded CSF flow or both constitute significant findings which indicate a need for treatment.

Yet another aspect of the invention provides methods of medical treatment comprising the steps examining a patient to detect abnormalities of the cranium, cervical spine or both capable of impeding cerebrospinal fluid flow. The method according to this aspect of the invention desirably includes the step of responding to detection of one or more of said abnormalities by performing at least one step selected from the group consisting of (i) treating the patient to alleviate or retard development of MS; and (ii) further monitoring the patient to detect incipient MS; and (iii) further monitoring the patient to monitor development of the abnormalities. Methods according to this aspect of the invention incorporate the realization that detection of abnormalities capable of impeding CSF flow can be useful in identifying patients who can benefit from further intervention. Merely by way of example, detection of such abnormalities following trauma such as an automobile accident can lead to useful clinical interventions which may prevent or mitigate MS.

Most preferably, the step of measuring CSF flow includes measuring CSF flow using MRI while the patient is in an upright position, and may also include measuring CSF flow using MRI while the patient is in a recumbent position. As used herein, the term "upright position" refers to a position of a patient in which the patient's spine extends generally vertically, and thus within 45 degrees of vertical, more typically within about 10-15 degrees of vertical as, for example, in a seated, reclining, or standing position. The term "recumbent position" refers to a position in which the patient's spine extends substantially horizontally, desirably within about 10-15 degrees of horizontal as, for example, in a supine position.

BRIEF DESCRIPTION OF THE DRAWINGS

FIGS. 1 and 1a-1h. are MR images of the neurological anatomy of a Multiple Sclerosis patient (Patient #1).

FIGS. 2a-2h. are MR images of the neurological anatomy of a Multiple Sclerosis patient (Patient #2).

FIGS. 3a-3f. are MR images of the neurological anatomy of a Multiple Sclerosis patient (Patient #3).

FIGS. 4a-4g. are MR images of the neurological anatomy of a Multiple Sclerosis patient (Patient #4).

FIGS. 5a-5g are MR images of the neurological anatomy of a Multiple Sclerosis patient (Patient #5).

FIGS. 6a-6g are MR images of the neurological anatomy of a Multiple Sclerosis patient (Patient #6).

FIGS. 7a-7f are MR images of the neurological anatomy of a Multiple Sclerosis patient (Patient #7).

FIGS. 8a-8f are MR images of the neurological anatomy of a Multiple Sclerosis patient (Patient #8).

FIGS. 9a-9c are MR images of the neurological anatomy of normal examinee #1 (i.e. without Multiple Sclerosis).

FIGS. 10a-10c are MR images of the neurological anatomy of normal examinee #2 (i.e. without Multiple Sclerosis).

FIGS. 11a-11c are MR images of the neurological anatomy of normal examinee #3 (i.e. without Multiple Sclerosis).

FIGS. 12a-12c are MR images of the neurological anatomy of normal examinee #4 (i.e. without Multiple Sclerosis).

FIGS. 13a-13c are MR images of the neurological anatomy of normal examinee #5 (i.e. without Multiple Sclerosis).

FIGS. 14a-14c are MR images of the neurological anatomy of normal examinee #6 (i.e. without Multiple Sclerosis).

FIGS. 15a-15c, are MR images of the neurological anatomy of normal examinee #7 (i.e. without Multiple Sclerosis).

FIG. 17 depicts the trauma history and pathological changes in cervical anatomy, CSF hydrodynamics and cinematography in seven Multiple Sclerosis patients and normal patients.

FIG. 18 depicts anatomic images, CSF flow images and CSF flow quantitation of Multiple Sclerosis patients.

FIG. 19 depicts anatomic images, CSF flow images and CSF flow quantitation of normal examinees (i.e. without Multiple Sclerosis).

DETAILED DESCRIPTION

Figure 1:
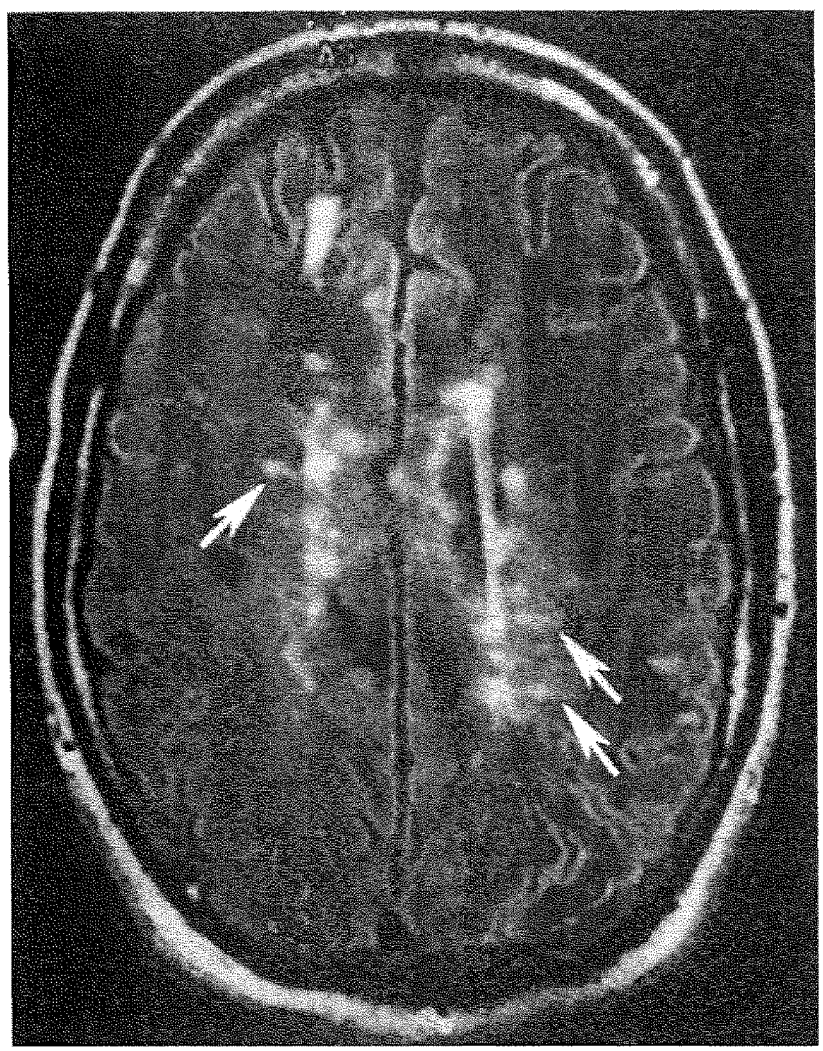

One apparatus which is capable of capturing MRI images and data with the patient in either a recumbent or upright position is sold under the registered trademark UPRIGHT® by Fonar Corporation of Melville, N.Y. Aspects of such apparatus are described in U.S. Pat. Nos. 7,123,008 and 6,677,753, the disclosures of which are incorporated by reference herein and copies of which are annexed hereto as Exhibits B and C. One parameter which can be measured is flow velocity of the CSF in the annulus of the spinal canal at a predetermined level. For example, the flow velocity can be measured at the axial mid-plane of the C-2 vertebrae. Known MRI algorithms commonly referred to as "phase-contrast imaging" can derive a measure of the fluid flow velocity within each voxel of an MRI data set. For estimation of total fluid flow, the flow velocities in a passageway such as the spinal annulus commonly are averaged over the entire cross-sectional area of the passageway. However, it has been found that the peak flow velocity, i.e., the maximum flow velocity observed in any one voxel in the imaged plane, provides a more sensitive measure. The inflow velocity, i.e., flow of CSF in the cephalid direction (towards the head) during left ventricular diastole, and the outflow velocity (the flow of CSF in the caudal direction, (away from the head) during left ventricular systole can be measured, preferably as peak values.

These or other values representing flow of CSF can be evaluated by a physician to determine if they demonstrated abnormal CSF flow. Such evaluation can be based on the physician's judgment and experience, with or without overt comparison to a standard or normal value. Where an overt comparison to a standard value is used, values indicating flow velocities greater than the standard or normal values indicate abnormal CSF flow. The standard or normal value used in such a comparison can be a standard or normal value for all patients or for a selected group of patients as, for example, for a group of patients selected by age, gender, ethnicity, physical activity level, height, weight or any combination of these characteristics.

Even without selection for these characteristics, there is a distinct difference between values seen in patients having active MS and values seen in normal patients. For example, as discussed in detail herein, the mean peak outflow value for patients having active MS is approximately 1.4, whereas the mean value for normal volunteers is on the order of 0.77. Thus, a value between these two values can be selected as a standard such that a value above about 1.1 cm/sec for peak outflow velocity in the upright position is taken as indicating obstructed CSF flow. Likewise, the mean value for peak inflow velocity for patients having active MS is about 0.55 cm/sec, whereas the mean value for normal volunteers is on the order of 0.34. Here again, any value between these mean values can be selected as a standard, but preferably a value of about 0.5 cm/sec is taken as the threshold between normal and impeded CSF flow. These threshold values can be adjusted upwardly or downwardly. Setting the threshold values closer to the values for normal subjects will increase the number of false positives, whereas setting the threshold values closer to the mean value for MS patients will increase the number of false negatives. However, the test still remains useful and predictive.

Many anatomical abnormalities can impede CSF flow. Examples of abnormalities which can impede CSF flow include cervical disc herniations and displacements; dislocations, fractures and degeneration of vertebrae such as cervical vertebrae; abnormal ligaments in the cervical spine as, for example, torn or stretched ligaments; abnormalities of the lordotic curvature; displacements or distortion of the spinal cord; and cerebellar tonsil ectopia or "CTE," also referred to as "Chiari syndrome." Anatomical abnormalities can be detected by imaging methods such as X-ray, CT scanning and MRI. MRI is particularly preferred inasmuch as it is capable of directly imaging tissues such as ligaments and discs. MRI imaging in an upright position, and most desirably in both recumbent and upright positions, are particularly preferred, inasmuch as such imaging can demonstrate abnormalities which cannot be seen in other modalities. The MRI imaging used to detect anatomical abnormalities optionally may be performed concurrently with MRI measurement of CSF flow.

Once a patient has been identified as having abnormal CSF flow CSF flow or as having an anatomical abnormality which may cause abnormal CSF flow, or both, the patient can be provided with intensive monitoring to detect indications of MS, can be treated immediately or both. For example, the patient can be treated to reduce intracranial CSF pressure (ICP), as by stenting a vein such as the azygous vein or the internal jugular veins, or by installation of a CSF drainage shunt from the ventricles to a location within the body outside of the skull, or by surgical removal of the anatomical abnormality which causes the abnormal CSF flow. Another modality which may be useful in reducing ICP is a shunt placed in the lumbar region of the spine. This procedure may be useful to prevent the CSF circulatory system from raising its pressure and thus raising the ICP. Lumbar shunts are likely to avoid many of the complications associated with ventriculoperitoneal (V-P) shunts.

Alternatively or additionally, the patient can be treated with other therapies known to alleviate the effects of MS or retard its progress. For example, it is known that administration of certain interferons early in the development of MS can retard development of the disease. Other agents such as certain immunosuppressants and monoclonal antibodies such as Natalizumab are known to have at least some effect in retarding the progress of MS or alleviating its effects. Pharmaceutical agents that reduce ICP may also be used. Monitoring to detect indications of MS can include conventional neurological evaluations. Initiating monitoring responsive to a finding of abnormal CSF flow, increased ICP, or both allows detection of incipient MS at an earlier stage, which in turn will allow initiation of treatment at an earlier stage. Moreover, initiation of monitoring or treatment responsive to a finding of abnormal fluid flow helps to focus monitoring or treatment efforts on those patients who are more likely to develop MS and thus helps to focus resources in a cost-effective manner. Conversely, in patients who already have known or suspected MS, detection of anatomical abnormalities which can cause abnormal CSF flow, or detection of abnormal CSF flow, indicates that intervention can retard further progress of the disease.

Non-invasive therapies such as Atlas Orthogonal treatment may also be useful in treating the causes and symptoms of MS. Such techniques may be useful because of their ability to correct cervical spinal abnormalities which may, improve the flow of CSF to the brain. Patients may also benefit by receiving any combination of these therapies (e.g. Atlas Orthogonal therapy and lumbar shunting.) Further aspects of the present invention are described in the numbered paragraphs set forth below.

Example 1

The present example is based on a study that originated in the course of performing UPRIGHT® MR images on a patient (patient #1, FIG. 1a) with an established diagnosis of MS. It was noted that one of the MS brain lesions conspicuously appeared to be arising directly from the CSF within the lateral ventricle (FIG. 1a arrow #1). This MS lesion, appearing to arise from the ventricular CSF, brought to our attention the unexplained tendency for MS lesions to be peri-ventricular in their distribution (2) (Figure I, and Figure II). Considered conjointly, an MS lesion appearing to arise directly from ventricular CSF (FIG. 1a) and the tendency of MS lesions to be peri-ventricular in their distribution (Figure I, Figure II) engendered the question whether abnormal CSF hydrodynamics (e.g., elevated intracranial pressure [ICP] or abnormal flow dynamics) was playing a role in the genesis of MS lesions. To address the question, eight patients with an established diagnosis of MS and seven normal examinees were studied in the FONAR UPRIGHT® Multi-Position™ MRI.

Patient #1 presented with what appeared to be parenchymally penetrating ventricular CSF and the newly available Phase Contrast (PCMR) MR technology for directly visualizing and quantifying CSF flow in both the upright and recumbent positions prompted further investigation of the role of CSF dynamics in Multiple Sclerosis.

The first eight MS patients who volunteered for the study were scanned and there was no specific criteria applied during the selection of the MS patients in this example. They were all scanned in the order in which they volunteered.

MRI scans were performed on a 0.6 T UPRIGHT® scanner (FONAR Corporation, Melville, N.Y.) with a quadrature head-neck combination coil. The patient bed can be rotated to any angle between the horizontal and vertical position in the space between the two poles of the upright magnet.

Regular clinical anatomical scans of the head and neck were acquired. Cine phase contrast scans of CSF flow were imaged using a phase contrast RF-spoiled gradient echo sequence with TR=19-22 ms, TE=9-12 ms, slice thickness=8 mm, flip angle=20-25°, matrix=256×128 zero filled to 256×256, and NEX=2. Data acquisition was retrospectively gated using ECG or pulse oximeter covering the entire cardiac cycle. Thirty-two (32) uniformly spaced time frames were obtained by linear interpolation in post-processing.

To visualize the overall CSF flow pattern, a single slice of FOV=26 cm was imaged in the midline sagittal plane. In order to quantify the CSF flow, an axial slice of FOV=16 cm at the mid C-2 level and perpendicular to the spinal canal was imaged (velocity encoding along the slice-select direction, venc=3-11 cm/s).

Quantification of CSF flow was accomplished by manually drawing the Region of Interest (ROI) around the spinal canal and spinal cord in the axial mid C-2 phase contrast scan. Phase offset was corrected by requiring the spinal cord to have zero net phase change over the whole cardiac cycle.

MR examinations of MS patients (FIGS. 1-8) and normal examinees (FIGS. 9-15) in the study were performed in both the upright and recumbent positions using the FONAR UPRIGHT® Multi-Position™ MRI. Examinees were deemed normal if they exhibited uninterrupted dorsal and ventral CSF flow on upright sagittal CSF flow images (e.g., FIG. 15c). MS patients #7 and #8 were unable to be scanned in the recumbent position. Lower limb paralysis prevented MS patient #7 from being scanned in the recumbent position, while severe vertigo and emesis in the recumbent position prevented MS patient #8 from being scanned in the recumbent position. CSF cinematography (ciné) was obtained both in the sagittal and axial planes. Quantitative MR measurements of CSF flow (cc/sec) through the spinal canal annulus obtained from axial MR images were calculated from the phase coded CSF flow image data. The flow data were obtained from axial images taken at the mid C-2 level, unless specified otherwise. The CSF velocity (cm/sec) was measured as the average annular proton velocity for each of the 32 imaging annuli acquired throughout the cardiac cycle. The peak CSF velocity was determined as the highest proton annular velocity measurement obtained for each phase (systole and diastole) of the cardiac cycle.

The pressure gradient was derived from the measured CSF velocity data using the Navier-Stokes equation, with negligible contribution from the viscous term. There were three notable findings.

MS patient #1 (FIG. 1a) presented with known peri-ventricular distribution of MS lesions (FIG. 1, II), and had abnormal CSF flows in all eight MS patients (FIGS. 1-8, Table 2A, col. 10). The abnormal CSF flows corresponded with the cranio-cervical structural abnormalities found on the patients' MR images. The second finding was a history of severe cervical trauma prior to the patient's MS diagnosis in six of the eight MS patients and a significant possibility of cervical trauma in a seventh patient (Table 1, MS patient #8). The third finding was the discovery that CSF inflow (cc/sec) and inflow velocity (cm/sec) in the upright position is about half (53-56%) (Table 3) of what it was in the recumbent position in both the MS patients and normal examinees.

It was initially noted that eight MS patients exhibited obstructions to their CSF flow when examined by phase coded CSF cinematography (ciné) in the upright position (Table 2A, col. 10 & 13). All MS patients exhibited CSF flow abnormalities that were manifest on MR cinematography as interruptions to flow or outright flow obstructions somewhere in the cervical spinal canal, depending on the location and extent of their cervical spine pathology (Table 2A, col. 10, 11 & 13). Normal examinees did not display these flow obstructions (Table 2B, col. 10 & 11).

Significant differences in MS patient CSF flow cinematography (ciné) in the sagittal midplane were observed between the upright and recumbent positions, while no positional differences in ciné flow were observed in normal examinees (Table 2B, col. 10, 11 & 13). CSF flow differences between the two positions were found in the six MS patients that were scanned both upright and recumbent (Table 2A, col. 10, 11 & 13). Obstructions of spinal CSF flow in both the dorsal and ventral spinal canals, when viewed sagittally, were found by cinematography in five of the eight MS patients when they were examined in the upright position (Table 2A, patients #1, #2, #3, #5 and #7, col. 10). Patient #3 exhibited both dorsal and ventral CSF flow obstruction only in the upright position (Table 2A, col. 10). Dorsal and ventral CSF flows in patient #3 were unobstructed in the recumbent position (Table 2A, col. 11).

Regarding the quantitation of CSF flow (cc/sec) abnormalities, determinations of peak CSF velocities (cm/sec) produced the most pronounced differences between the MS patients and normal examinees (Table 2A, col. 2, 3, 4, & 5). While the peak velocity measurements in our study were measured differently than the peak velocities by Haughton et al. [Haughton et al. (4) determined the peak velocity to be the highest voxel velocity measured in the scan as compared to the highest annular velocity measured in the scan in our determination], both peak velocity methods found the peak velocity determination to be the most sensitive measure for detecting CSF flow abnormalities.

Among the MS patients, three of the eight patients had significantly ($P<0.05$) elevated peak CSF outflow (systolic) velocities (cm/sec) from the brain (2.58, 1.80, 2.03 cm/sec) in the upright position (Table 2A, col. 2, patients #2, #4 and #5) compared to the mean value for the normal examinees in the upright position (0.893±0.32 cm/sec, Table 2B, col. 2). Outflow velocities for all three of these MS patients were more than twice the upright outflow peak velocities for the normal examinees. Four (patients #1, #2, #4, and #5) had significantly elevated peak CSF outflow velocities (cm/sec) (1.52, 1.39, 2.71 and 2.14 cm/sec, Table 2A, col. 3) in the recumbent position, two of which (2.71 and 2.14 cm/sec) were more than twice the normal value (0.896±0.17 cm/sec, Table 2B, col. 3). A fifth MS patient (patient #3) had a recumbent CSF outflow velocity of 0.336 cm/sec that was significantly reduced relative to normal (0.896±0.17 cm/sec).

In addition, two of the eight MS patients (Table 2A, col. 4, patients #2 and #5) exhibited significantly elevated peak inflow velocities in the upright position (Table 2A, col. 4, 1.047, and 0.731 cm/sec) relative to the peak inflow velocities of normal examinees (0.400 cm/sec) in the upright position (Table 2B, col. 4). Importantly, therefore, five of the eight MS patients had at least one significantly abnormal peak CSF velocity measurement in three of the parameters measured (upright outflow, recumbent outflow, and upright inflow), and three of the MS patients exhibited elevated peak velocities in both the upright and recumbent positions (patients #2, #4, and #5, Table 2A, col. 2 & 3).

Additionally it was found that peak CSF inflow (1.023 cc/sec) and peak CSF inflow velocity (0.400 cm/sec) (Table 3) were sharply reduced in normal examinees in the upright position when compared to inflow and inflow velocity in the recumbent position. Both peak inflow (cc/sec) and peak inflow velocity (cm/sec) in the upright position were found to be about half (53%-56% respectively), of what they were in the recumbent position (Table 3) in the normal examinees. Except for patient #2 and normal examinee #5, both MS patients and the normal examinees exhibited reduced inflow velocity in the upright position (Table 2A, col. 4 & 5; Table 2B, col. 4 & 5). In the case of patient #2, the anticipated velocity reduction arising from the upright position was offset by the peak velocity acceleration arising from the patient's pathology (Table 2A, col. 4 & 8).

This striking reduction of CSF inflow into the brain in the upright position in both MS patients (Table 2A) and normals (Table 2B, Table 3) was unexpected, inasmuch as cerebral blood flow in normal subjects is unaffected by position (5). The observed reduction in CSF inflow in the upright position apparently constitutes normal physiology. The unexpected observation that CSF flow is significantly reduced in the upright position (or significantly increased in the recumbent position) raises interesting questions regarding the physiological significance of the increased CSF flow of recumbency.

Another unexpected finding was the high percentage of "normal" adults that presented with underlying spinal abnormalities. It was found that a large percentage of normal examinees (as high as 75%) did not qualify as normal with respect to their cervical spine anatomy, e.g., exhibiting localized disc herniations (or significant bulges) at C5/6 or elsewhere, or localized interruptions of CSF flow. Such examinees were entirely asymptomatic currently and historically, but were nonetheless unable to meet a standard for normal cervical spine anatomy. With the cervical spine being the most active segment of the spine, the finding, though unexpected, is not inconsistent with the cervical spine's high degree of biomechanical activity.

Since one of the physiological roles attributed to the CSF is the delivery of nutrients to the brain and the removal of toxic metabolic waste, the increase in CSF flow facilitated by recumbency engenders the consideration that the normal nocturnal sleep process may in fact be playing an active role in facilitating the removal of metabolic waste from the brain and delivering nutrients. Recumbent sleep may be enabling increased CSF inflow into the brain for the physiologic purpose of delivering nutrients to the brain and cleansing it of toxic metabolic by-products*. Similarly, it may account, in some measure, for the benefits of recumbent sleep in the medical healing process.

Cranio-Cervical Trauma and Abnormal CSF Hydrodynamics in MS 11

TABLE 3

Change of CSF Inflow With Position in Normal Examinees
(see Tables 2A and 2B for velocities)

| 1<br>Peak<br>INFLOW<br>(cc/sec)<br>UPRIGHT | 2<br>Peak<br>INFLOW<br>(cc/sec)<br>RECUMBENT | 3<br>Peak<br>INFLOW<br>Velocity<br>(cm/sec)<br>UPRIGHT | 4<br>Peak<br>INFLOW<br>Velocity<br>(cm/sec)<br>RECUMBENT |
|---|---|---|---|
| 1.023 | 1.935 | .400 | .715 |
| % Difference Up/Rec<br>53% | | % Difference Up/Rec<br>56% | |

Another unexpected finding was that of the eight Multiple Sclerosis patients, six had a prior history of severe trauma to the neck (Table 1, col. 2) with one patient (patient #2) having sustained both neck and head trauma. In addition, there is a significant likelihood that trauma had a role in the genesis of a seventh patient's MS (Table 1, patient #8, col. 2). As the data discussed herein demonstrates, prior trauma may be a causative factor in the onset of MS. This is particular true in the case of trauma involving the head and neck. FIG. 17 is labeled as Table 1 and shows the trauma history and pathological changes in cervical anatomy, CSF hydrodynamics and cinematography in seven MS patients and normals. FIG. 18 is labeled as Table 2A and shows anatomic images, CSF flow images and CSF flow quantitation of MS patients. FIG. 19 is labeled as Table 2B and shows anatomic images, CSF flow images and CSF flow quantitation of normal examinees.

All seven patients had distinct cervical anatomic pathology on their current MR images that corresponded with their trauma histories, thereby establishing that the historical trauma events contributed directly to their permanent pathologies of the cervical spine (Table 2A, col. 8 & 9) and that their cervical trauma histories were not immaterial. Four had received neck injuries in motor vehicle accidents, three of which were whiplash injuries, and the fourth a "reverse whiplash" (neck flexion preceding neck extension) injury (patient #7). A fifth, patient #8, was involved in a severe motor vehicle accident at age 2-3 that "totalled" the car in which she was riding without a seat belt or infant seat.

Noteworthy was the fact that the trauma and particularly motor vehicle trauma, notwithstanding its severity, was never correlated by either the patients or their physicians with the onset of their MS symptomatology. The symptoms of head and neck trauma, however, can be long lasting (e.g., 17 yrs.) (9). In all but two of the patients (patients #2 and #7, Table 1, col. 4) the trauma preceded the onset of MS symptoms by more than 8 years. When the mean value was calculated for all eight MS patients, the average number of years the patient's trauma preceded the patient's MS diagnosis, was 11 years. In addition, the abnormal CSF flow dynamics found in the MS patients of this study corresponded to the MR cervical pathology that was visualized (Table 2A, col. 2-9).

In the UPRIGHT® MRI examination of the eight MS patients, four of the eight exhibited severe cervical anatomic pathology (patients #1, #2, #3 and #7, Table 2A, col. 8). The remaining four patients had less severe but still serious cervical anatomic pathology (Table 2A, col. 8) and two (MS patients #2 [FIG. 2] and #8 [FIG. 8]) exhibited conspicuous swelling of the body of the cerebral lateral ventricles or of the occipital horns of the lateral ventricles.

In all but one (patient #6) of the seven MS patients that were imaged in both the upright and recumbent positions, the visualized anatomic pathology was more severe in the upright position than in the recumbent position (Table 2A, col. 8 & 9). Patient #1, for example, exhibited a 16° mal-rotation of C-2 on the patient's upright axial image (FIG. 1e) FIG. 1b-1h. The first MS patient (patient #1) exhibited peri-ventricular MS lesions (FIGS. 1g & 1h) that were adjacent to the occipital horns of the lateral ventricles as well as to the anterior horns. Additionally, MS patient #1 exhibited a non-uniform distribution of peri-ventricular interstitial edema (PVIE). Peri-ventricular interstitial edema suggestive of CSF leakage was present anterolaterally in both right and left lateral ventricles in the axial image of FIG. 1h (black arrows) and was most pronounced adjacent to the anterior horn of the right lateral ventricle (FIG. 1g black arrow). The patient also exhibited a sixteen degree (16°) counter-clockwise rotation of C2 in the upright position (FIG. 1e white arrow) which reduced to a five degree (5°) rotation in the recumbent position (FIG. 1f). Additionally, disc herniations and disc protrusions were observed to be present in the upright position at all cervical levels from C2/3 to C6/7 (FIG. 1b) with the most prominent protrusions/herniations occurring at C4/5, C5/6, and C6/7 abutting the spinal cord and obstructing the ventral spinal canal. The disc herniation and cord abutment at C6/7 was the most pronounced (FIG. 1b white arrow). An impediment to dorsal CSF flow manifest as hypertrophy and infolding of the ligamentum flava at C2/3 and C3/4 dorsally (FIG. 1b black arrow) was also visualized.

The visualized anatomic obstructions of the dorsal and ventral spinal canals resulted in corresponding dorsal and ventral interruptions of CSF flow in the spinal canal (FIG. 1c). Axial CSF flow measured in the recumbent position at C4 was interrupted from 1 o'clock to 6 o'clock in the left lateral spinal canal (FIG. 1d white arrow).

Figure 1A:
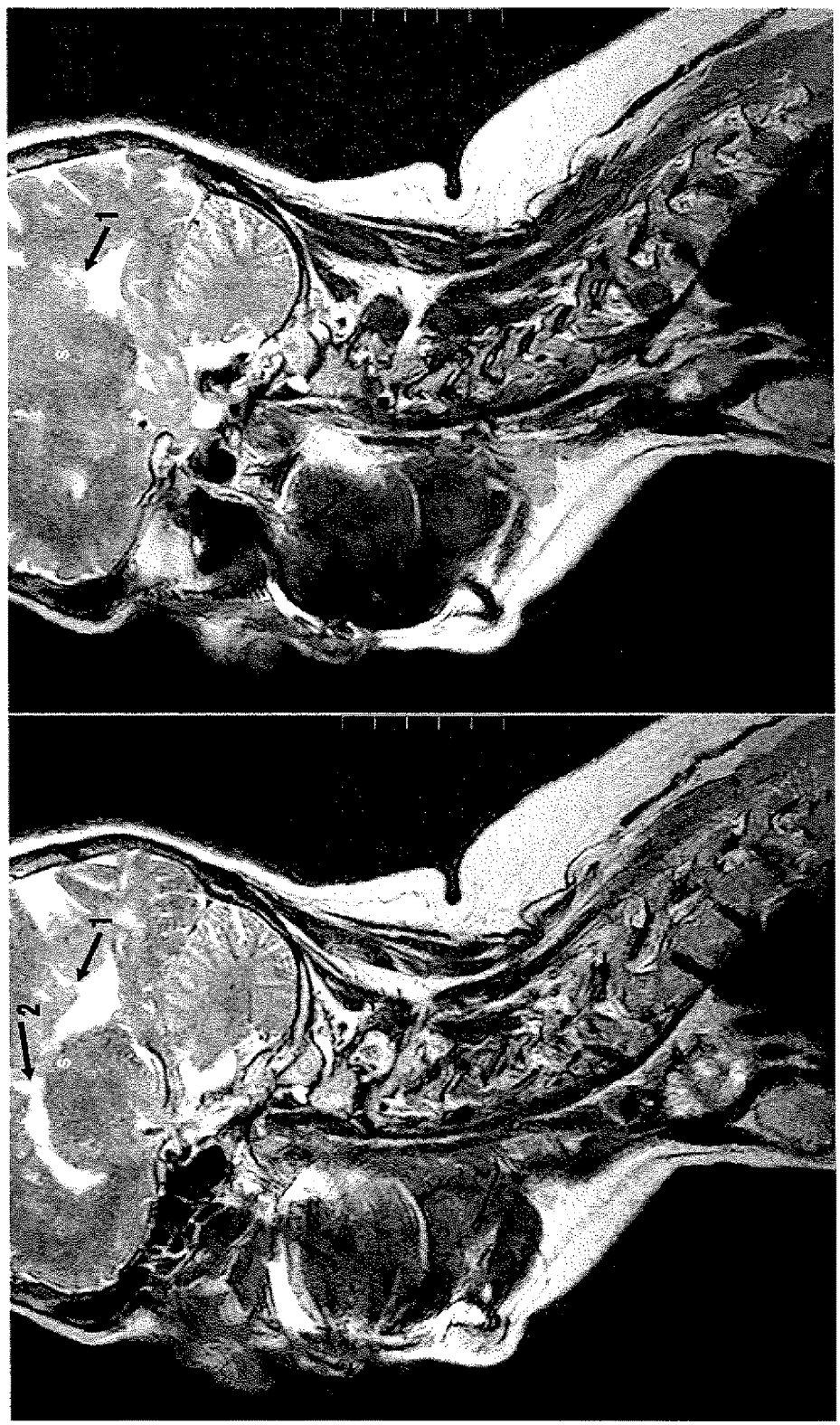

In FIGS. 1 and 1a, a Sagittal T2-weighted image of a Multiple Sclerosis patient (patient #1) showing two peri-ventricular MS plaques (arrows 1 & 2 in FIG. 1a) perpendicular to the ventricular wall. Lesion 1 (arrow 1) exhibits an explicit connection between ventricular CSF and an MS plaque. Lesion 2 exhibits a similar connection to ventricular CSF but in a less striking manner. The images visualizing the CSF "leaks" of FIGS. 1 and 1a were obtained on Mar. 11, 2010 with the patient upright in the FONAR UPRIGHT® Multi-Position™ MRI.

Figures 2A, 2B:
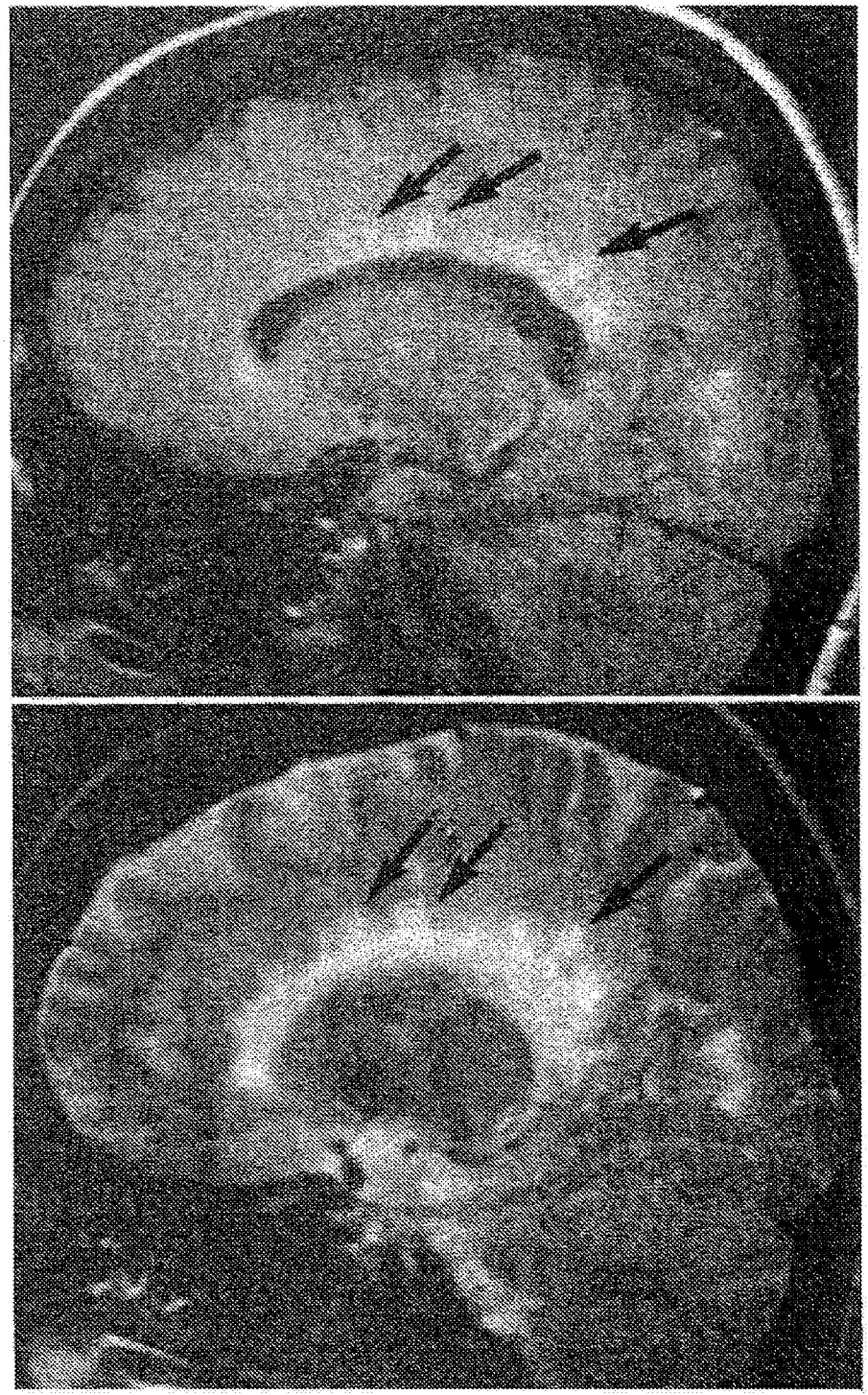

In FIGS. 2a-2h, MS patient #2 exhibited MS lesions adjacent to both occipital horns of the lateral ventricles (FIG. 2e black arrows), MS lesions adjacent to both anterior horns (FIG. 2e) and hydrocephalus of the lateral ventricles (FIG. 2d) and (FIG. 2f white arrow). The presence of non-uniform peri-ventricular interstitial edema at the anterior horns was also evident (FIG. 2e white arrow). Anatomically, cerebellar tonsil ectopia (CTE) was seen abutting the brainstem (FIG. 2d white arrows) and was manifest as incomplete and dorsally obstructed CSF flow in the posterior foramen magnum secondary to cerebellar tonsil obstruction (FIG. 2d white arrows). Additionally, anatomic impedance and obstruction of CSF in the ventral spinal canal (FIG. 2h opposite white arrow) was visualized at C5 and C4 secondary to a posterolisthesis of C5 and a disc herniation abutting and posteriorly displacing the spinal cord at C5/6. The anatomic CSF obstruction of the ventral spinal canal visualized in the patient's upright sagittal image of the cervical spine (FIG. 2h opposite white arrow) was manifest as corresponding impairments of CSF flow ventrally and dorsally from C4 to C5 (FIG. 2g black arrows).

In FIGS. 3a-3f, MS patient #3 exhibited an MS lesion adjacent to the occipital horn of the left lateral ventricle (FIG. 3d black arrow) and enhanced peri-ventricular interstitial edema at the anterior horns (white arrow). Anatomical degradation of cervical vertebra C4 and C5 and obstructive disruption of the spinal canal at this level is visualized in the upright image of the cervical spine (FIG. 3a). Dorsal and ventral CSF flow is likewise interrupted at C4 and C5 (FIG. 3b long white arrows). Dorsal and ventral CSF flow is unobstructed anatomically at C2 (FIG. 3a) in the upright position and unobstructed both sagittally (FIG. 3b short white arrows) and axially (FIG. 3e) with respect to CSF flow in the upright position. In the recumbent position, however, CSF flow is obstructed dorsally at C2 (FIG. 3f white arrow), in contrast to unobstructed dorsal CSF flow at C2 when the patient is upright (FIG. 3e). CSF flow in the recumbent position (FIG. 3c white arrowhead), however, is also obstructed ventrally at the same C4 and C5 cervical levels that exhibit the anatomic disintegration visible in the upright MR images of the patient's cervical spine (FIG. 3a).

In FIGS. 4a-4g, MS patient #4 exhibited a pronounced aggregate of MS lesions in peri-ventricular distribution around the lateral ventricles (FIGS. 4d and 4c) increasing in frequency in the direction of the occipital horns (FIG. 4d black arrow). Irregular peri-ventricular interstitial edema is pronounced at the anterior horns (FIG. 4c short white arrow). The density of MS lesions is most pronounced adjacent to the occipital horns (FIG. 4c) where, in addition, what appears to be a CSF "leakage" striation (FIG. 4c) arising from the right occipital horn (white arrow) is conspicuous and suggestive of an increase in ventricular CSF pressure within the lateral ventricle. Patient #4 also exhibits a posterior displacement of the spinal cord within the spinal canal abutting the posterior wall of the spinal canal (FIG. 4a) at the level of cervical disc C3/4 (white arrow). The anatomic obstruction of the dorsal spinal canal resulting from the posterior displacement of the spinal cord and its abutment of the posterior wall of the canal (FIG. 4a), is accompanied by an obstruction of dorsal CSF flow in the spinal canal (FIG. 4b black arrow). Axial MR images of the spinal canal taken in both the upright position (FIG. 4f) and in the recumbent position (FIG. 4g) exhibit a corresponding absence of dorsal CSF flow in the upright position (FIG. 4f) at the mid C-4 level (FIGS. 4e and 4f) and also at the mid C-3 level in the recumbent position (FIG. 4g).

In FIGS. 5a-5g, MS patient #5 exhibited peri-ventricular MS lesions (FIG. 5e white arrows) on the upright sagittal FLAIR images of the brain. The upright axial FLAIR images (FIGS. 5g and 5f) show MS lesions adjacent to the left occipital horn of the lateral ventricle (FIG. 5g black arrow) and lesions attached to the lateral wall of the left ventricle (FIG. 5f white arrow). Additionally, irregular peri-ventricular interstitial edema is present most pronounced in the right occipital horn (FIG. 5g black arrow), with the additional suggestion of CSF "leakage" (FIG. 5g small black arrow) suggestive of an increase in intraventricular CSF pressure connecting the left occipital horn to the MS lesion. Anatomically, MS patient #5 exhibited cervical disc bulges indenting the thecal sac and anatomically interfering with CSF flow at C4/5, C5/6 and C6/7 (FIG. 5a). Direct cervical disc abutment of the spinal cord is exhibited at C5/6. Correspondingly, CSF flow is interrupted ventrally at C2/3, C3/4, C4/5, C5/6 and C6/7 in the upright sagittal images of CSF flow (FIG. 5b). Additionally, significant compromise of the dorsal spinal canal at C2/3 (FIG. 5a white arrow) that appears obstructive of CSF is manifest as an obstruction and absence of CSF flow dorsally from C2/3 to C6/7 (FIG. 5b white arrow). The axial image of CSF flow obtained at mid C-3 (FIG. 5c) exhibits an absence of CSF flow dorsally but satisfactory ventral flow (FIG. 5c white arrow) corresponding with the upright CSF flow imaging of the sagittal plane that exhibits disc interrupted ventral CSF flow but absent dorsal CSF flow (FIG. 5b white arrow). The recumbent axial imaging of CSF flow (FIG. 5d) exhibits increased annular flow compared to CSF flow in the upright position at C3 (FIG. 5c) but the same annular distribution of CSF flow that shows intact ventral flow but absent dorsal flow.

In FIGS. 6a-6g, MS patient #6 exhibited an MS lesion proximate to the wall of the left lateral ventricle (FIGS. 6f & 6g white arrows). CSF flow in the dorsal spinal canal is unobstructed anatomically in the upright position (FIG. 6a) and correspondingly unobstructed in the dynamic images of dorsal CSF flow (FIG. 6b black arrow). Obstruction of ventral CSF flow (FIG. 6b white arrow) in the upright position corresponding to the cervical disc herniations (FIG. 6a) that obstruct the ventral spinal canal and abut the spinal cord is evident in FIG. 6b. The cervical disc herniations at C3/4, C4/5 and C5/6 responsible for the obstruction are visualized in the upright T2 image of the cervical spine (FIG. 6a black arrows) where they are seen indenting the thecal sac abutting the cord and anatomically obstructing the CSF ventrally (FIG. 6a). The ventral CSF flow obstruction of MS patient #6 is visible only with the patient upright. When weight loading of the C-spine is removed with the patient in the recumbent position (FIG. 6c), CSF flow is restored ventrally and both normal dorsal and ventral CSF flow are simultaneously visualized (FIG. 6c black arrows).

In FIGS. 7a-7f, MS patient #7 exhibited MS lesions adjacent to the left occipital horn (FIGS. 7f & 7e black arrows) and proximate to the right occipital horn (FIGS. 7d & 7e small black arrow). Additionally, striations suggestive of CSF "leakages" appear in the upright axial FLAIR images of patient #7 (FIGS. 7f, 7e and 7d white arrows). Also present is an irregular peri-ventricular interstitial edema suggestive of increased intracranial pressure that is exhibited as hyperintensities contiguous with the anterior horns of the lateral ventricle. The hyperintensity is most pronounced contiguous with the right anterior horn of the lateral ventricle (FIG. 7e anterior white arrow). The peri-ventricular edema is also visible contiguous with the lateral walls of the left and right anterior horns of the lateral ventricles (FIG. 7d anterior white arrows). Anatomically severe compression of the spinal cord is visible in MS patient #7 from C2/3 to C5/6 obstructing the ventral spinal canal. The disc compressions of the cord (FIG. 7a) are further compounded by an additional retrolisthesis of C5 when the patient is upright (FIG. 7b) that compresses the cord further and displaces it posteriorly to a greater extent in the upright position (FIG. 7b white arrow) under the added weight load. Additionally, hypertrophies of the ligamentum flavum (FIG. 7b intersecting white arrows) compress the spinal cord dorsally and obstruct the dorsal canal (FIG. 7a). The dynamic upright imaging of CSF flow (FIG. 7c) exhibits a corresponding obstruction of CSF flow dorsally (FIG. 7c black arrow) from C2/3 to C4/5 and impairs CSF flow ventrally in the same region.

In FIGS. 8a-8f, MS patient #8 exhibited a pronounced peri-ventricular distribution of MS lesions (FIG. 8a). In addition, multiple cerebral pathologies suggestive of increased intracranial pressure (ICP) were seen. Most conspicuous was the hydrocephalus of the occipital horns of the lateral ventricles visualized in the Upright T2 axial images of the brain (FIG. 8e white arrow) and in axial Flair images of the brain (FIG. 8f). Particularly prominent was the pronounced edema seen adjacent to the occipital horns of the lateral ventricles (FIG. 8f black arrows) strongly suggestive of CSF "leakage", possibly secondary to an increased ICP, into the surrounding brain parenchyma. Similarly, the conspicuous collar of interstitial edema surrounding the lateral ventricles in the upright Flair sagittal image of the brain (FIG. 8c) and the conspicuous ventricular dilatation of the body of the lateral ventricles (FIG. 8b white arrow) are further suggestive of an increased intracranial pressure (ICP) being the origin of the CSF "leakage" seen in FIGS. 8e and 8f.

In FIGS. 9a-9c, UPRIGHT® normal examinee #1 exhibits continuous ventral and dorsal sagittal CSF flow (FIGS. 9a & 9c black channels) as well as uninterrupted 360° annular circumspinal flow (black annulus) visualized in the axial image obtained at mid C-2 (FIG. 9b).

In FIGS. 10a-10c, UPRIGHT® normal examinee #2 shows full patency of the ventral and dorsal spinal canals (FIG. 10a) manifest as uninterrupted ventral and dorsal sagittal CSF flow (FIG. 10b black channels) and as uninterrupted 360° annular circumspinal CSF flow in the axial image obtained at mid C-2 (FIG. 10c black annulus).

In FIGS. 11a-11c, UPRIGHT® normal examinee #3 exhibits patient ventral and dorsal spinal canals (FIG. 11a) confirmed by intact ventral and dorsal CSF flow in upright sagittal CSF flow (FIG. 11b black channels) and full 360° annular circumspinal CSF flow in the axial image obtained at mid C-2 (FIG. 11c black annulus).

In FIGS. 12a-12c, UPRIGHT® normal examinee #4 exhibits patient ventral and dorsal spinal canals (FIG. 12a) with full UPRIGHT® ventral and dorsal CSF flow (FIG. 12c black channels) and full 360° annular circumspinal recumbent CSF flow in the axial image obtained at mid C-2 (FIG. 12b black annulus).

In FIGS. 13a-13c, UPRIGHT@ normal examinee #5 exhibits patient ventral and dorsal spinal canals (FIG. 13a) visualized as uninterrupted UPRIGHT@ CSF flow ventrally and dorsally in the sagittal CSF image (FIG. 13b black channels) as well as in full 360° annular circumspinal CSF flow in the UPRIGHT@ axial image obtained at mid C-2 (FIG. 13c black annulus).

In FIGS. 14a-14c, UPRIGHT® normal examinee #6 exhibits patient ventral and dorsal spinal canals (FIG. 14a) confirmed by uninterrupted ventral and dorsal CSF flow in the UPRIGHT® sagittal image of CSF flow (FIG. 14c black channels) and by full 360° annular circumspinal CSF flow in the axial recumbent image obtained at mid C-2 (FIG. 14b black annulus).

In FIGS. 15a-15c, UPRIGHT® normal examinee #7 exhibits patient ventral and dorsal CSF channels (FIG. 15a) confirmed by full 360° annular circumspinal CSF flow in the UPRIGHT® axial image obtained at mid C-2 (FIG. 15b black annulus) and by the uninterrupted ventral and dorsal CSF flows exhibited in the UPRIGHT® sagittal CSF flow study (FIG. 15c black channels).

Figure 16B:
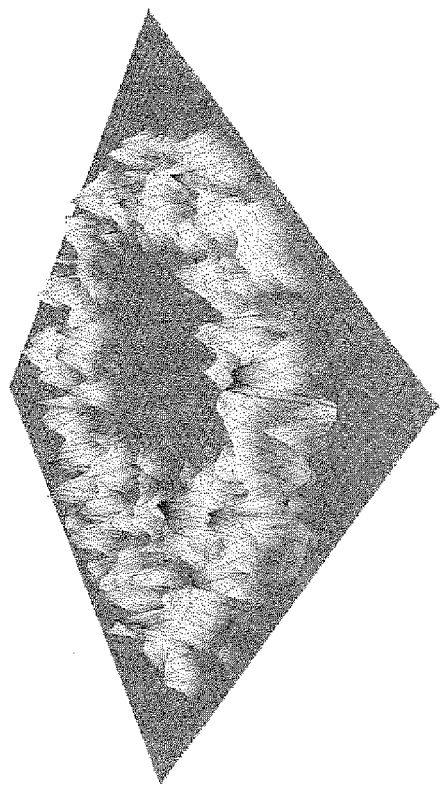
FIG. 16b is an image of pixel* velocity maps of CSF from the patient in FIG. 16a, after treatment.
Figure 16A:
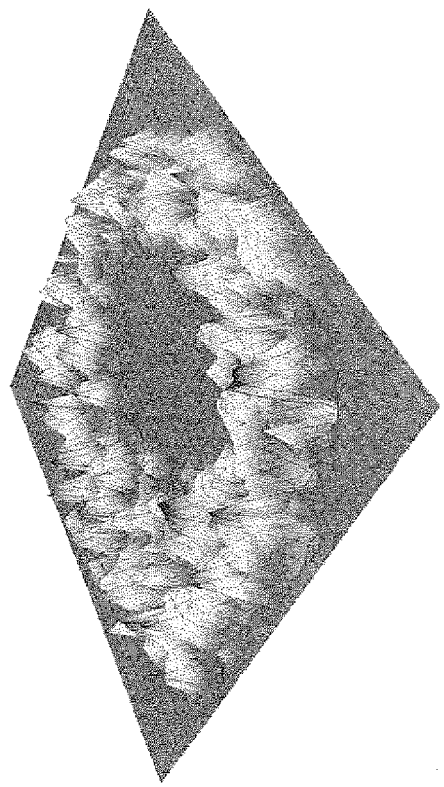
FIG. 16a is an image of pixel* velocity maps of CSF in the peri spinal CSF annulus at mid C-2 in an upright symptomatic patient prior to treatment.

In FIG. 16a are the pixel* velocity maps of CSF in the peri-spinal CSF annulus at mid C-2 in the upright symptomatic patient prior to treatment.

In FIG. 16b exhibits an overall reduction in CSF velocity as well as a distinct reduction in the number of CSF flow jets (red), compared to the number of flow jets present in the symptomatic patient prior to treatment (FIG. 16a) that reduced to a 5.7° rotation (FIGS. 1e & 1f) when the patient was recumbent. Another example is patient #2. In patient #2, the spinal canal stenosis in the upright position at C5/6 (FIG. 2f opposite white arrows; Table 2A, col. 8), that was the result of disc herniation, osteophyte compression and retrolisthesis of C-5 obstructing the anterior spinal canal, was further compounded in the upright position by anterior infolding of the ligamentum flavum obstructing the dorsal spinal canal at C5/6 and at C6/7. The canal stenosis in patient #2 was substantially reduced in the recumbent position where the ligamentum flavum infolding became non-existent and non-obstructive of the dorsal spinal canal when the patient was recumbent (Table 2A, col. 8 & 9). See Table 2A, col. 8 & 9 for the remainder of the important differences in anatomic pathology in the upright and recumbent positions. Similarly, obstructions of CSF flow were more pronounced in the upright position than in the recumbent position (Table 2A, col. 10 & 11).

Upright (and recumbent) MR images of the MS patients and normal examinees are presented in FIGS. 1-16.

The compared upright and recumbent MR imaging findings of the brain and cervical spine of the Multiple Sclerosis patients are described in FIGS. 1-8. The MR images of the normal examinees are contained in FIGS. 9-15.

As described in FIGS. 1-8, all MS patients exhibited specific anatomic pathologies of the cervical spine and corresponding obstructions of CSF flow. Four of the MS patients (MS patients #1, #2, #3 and #7) exhibited severe anatomic pathology, while the remaining four (MS patients #4, #5, #6 and #8) exhibited less striking cervical spine anatomic pathology that was nonetheless accompanied by significant obstructions to CSF flow (patient #4, FIGS. 4b, 4f, 4g: patient #5, FIGS. 5b, 5c, 5d: patient #6, FIGS. 6b, 6e) which CSF flow obstructions could result in increases in ventricular intracranial pressure (ICP), CSF leakages and the genesis of MS lesions. Additionally, the hydrocephalus of the occipital horns of the lateral ventricles (FIG. 8e) and the ventricular dilatation of the body of the lateral ventricles (FIG. 8b) are consistent with the likelihood of an increased ICP in patient #8.

The findings raise the possibility that interventions might be considered to restore normal intracranial CSF flow dynamics and intracranial pressure (ICP) as well as surgical procedures to correct the causative anatomy if non-invasive procedures prove insufficient.

Accordingly, the elevated peak CSF velocities measured in the MS patients of this study may indicate the existence of elevated intracranial pressures (ICP) in these MS patients.

Additionally, three of the eight MS patients (Table 2A, col. 6 & 7, patients #2, #4 and #5) directly exhibited elevated peak-to-peak CSF pressure gradients by MRI. Accordingly, the increases in the peak-to-peak pressure gradients of these MS patients and the accompanying ICP increases can directly be the origin of the CSF "leaks" that appear evident in MS patient images and evident in their peri-ventricular distribution (FIG. 1a, Figures I, II). Consistent with the findings of Struck and Haughton (10), the MS patients of this study who exhibited elevated CSF peak inflow velocities in the upright position (Table 2A, col. 4, patients #2 and #5, 1.047, 0.731) also exhibited elevated peak-to-peak pressure gradients when upright (Table 2A, col. 6, 0.054, 0.050 mmHg/cm) as compared to the normal examinees (Table 2B, col. 6, 0.0177).

The existence of peri-ventricular interstitial edema, FIGS. 1-8, in the MR images of the brain of all eight of the MS patients of this study is further consistent with the prospect that an increase in ICP is playing a role in generating MS "plaque" lesions.

The most important finding of this study is that cerebrospinal fluid "leaks" from the ventricles of the brain into surrounding brain parenchyma, possibly secondary to trauma induced blockages of CSF flow and resulting increases in ICP, may be playing an important etiologic role in the genesis of Multiple Sclerosis. The existence of such possible CSF "leaks" contributing to MS plaque formation could not be known until MS plaques themselves became readily visible on medical images. The advent of MRI made this a reality (1). Such CSF "leaks" could not have been seen prior to MRI, and a role for CSF "leakage" in the genesis of MS could not have been known prior to the advent of MRI and prior to the availability of phase coded MR imaging. These combined technologies have now made CSF flows directly visible and quantifiable.

The first suggestion of this possibility arose from the T2 weighted sagittal brain image of a patient with MS (FIG. 1a, patient #1) displaying an explicit CSF connection between ventricular CSF and one of the patient's MS lesions (FIG.

1a, arrow #1). Another lesion in the same image exhibits a similar direct connection to ventricular CSF but in a less striking manner (FIG. 1a, arrow #2).

Consistent with the possibility that MS plaques originate as CSF "leaks" secondary to trauma, is the existence of Dawson's fingers (Figure I) where the "long axis of the (MS) plaque" is "parallel with the white matter fibers in the corona radiata", i.e., not within the white matter fibers themselves but parallel to them. "Dawson's fingers" might well be the "leak" pathways of cerebrospinal fluid originating in the ventricle and joining the body of the MS plaque within the brain parenchyma. Parallel to the white matter fibers would be the path of least resistance for "leaking" CSF to diffuse within the brain parenchyma, i.e., alongside the white matter fibers. These findings may explain why MS lesions are not distributed throughout the while matter of the brain, but are instead clustered around the ventricles.

Protein is the principal ingredient, other than water, of the cerebrospinal fluid. CSF contains approximately 15 to 40 mg/dL of protein). CSF gel electrophoresis has established that there are "more than 300 polypeptides in CSF". In addition, "nine antigenic species have been demonstrated in CSF that are absent in serum" The question naturally arises whether the "leakage" of these CSF antigenic proteins, like the antigenic tau proteins they are known to contain, could be the source of the antigens generating the autoimmune reactions known to be the origin of MS lesions.

If trauma induced "leakage" of CSF proteins into the surrounding brain parenchyma, and particularly "leakage" of antigenic proteins, contributes to the formation of MS plaques, then the vascular expansion stenting of the Azygous and Internal Jugular Veins could be monitored after installation by UPRIGHT® phase coded MRI measurements of CSF flow. Upright phase coded imaging of CSF flow would assure that installed expansion stents are achieving the corrections of CSF flow dynamics and intracranial pressure (ICP) that are needed to terminate plaque generating CSF "leaks".

It is possible that those patients who currently do not respond to the Azygous and Internal Jugular vein expansion stents or those who relapse are relapsing or not responding because the necessary restoration of normal CSF hydrodynamics and normal ICP has not been fully accomplished by the initial venous stenting procedure or is not being maintained.

Since tau proteins are a normal component of CSF, the "leaks" of ventricular CSF (FIGS. 1a, I, II, 1g, 1h, 2c, 3d, 4c, 4d, 5f, 5g, 7d, 7e, and 7f), secondary to trauma, may be the origin of the antigenic tau proteins found in these repetitive head trauma patient. In addition, the tau proteins have been identified as a significant participant in Alzheimer's disease. The possibility that they too are originating in the ventricular CSF, possibly secondary to increases in ICP, raises the prospect that Alzheimer's may also be the result of pathologic CSF hydrodynamics, which if corrected could halt the progress of Alzheimer's symptoms. [Accordingly, while multiple authors have fruitfully called attention to the correlation between trauma and the onset of MS, perhaps the "missing link" to date has been the inability to directly "see" the CSF "leaks" and CSF flow obstructions that have now been made visible by phase coded MR imaging.] This new power to dynamically visualize CSF hydrodynamics and its abnormalities opens the prospect of medically restoring pathologic CSF flow dynamics to normal under MR image guidance, thereby eliminating pathogenetic CSF leakages and the symptomatologies to which they give rise.

Myelogenesis is a normal physiologic process that repairs damaged myelin over time. If the myelin injuring process, i.e., "leaked" antigenic CSF proteins, could be terminated, there is the possibility that with the continuing injury from CSF "leakage" terminated, the demyelinated axons of MS lesions could be remyelinated by normal physiologic myelogensis and the MS lesions repaired.

The findings further suggest that going forward, victims of motor vehicle whiplash injuries with persisting symptoms (e.g., headache, neck pain) should be scanned by UPRIGHT® MRI to assure that their CSF hydrodynamics and cervical anatomy (C1-C7) are normal. Should their CSF hydrodynamics prove abnormal, they should be monitored by UPRIGHT® MRI to assure they are restoring to normal over time, or ultimately decompressed by expansion stenting or cervical realignment if they are not.

The malalignment of C-1 found by the FONAR UPRIGHT® MRI images of the cervical spine of MS patient #8 in the upright position was successfully treated, using Atlas Orthogonal (AO) instrumentation. Patient No. is the first MS patient of this study of MS patients treated thus far. The patient's symptoms, severe vertigo accompanied by vomiting when recumbent and stumbling from unequal leg length, ceased upon treatment. FIG. 16a is the pixel* velocity map of CSF in the peri-spinal CSF annulus at mid C-2 in the upright symptomatic patient prior to treatment. The CSF void in the center is the spinal cord. FIG. 16b is the pixel velocity maps of the upright asymptomatic patient immediately following treatment with the AO instrument. Pixel velocities were obtained from the axial CSF flow MR images obtained at C-2. FIG. 16b exhibits an overall reduction in CSF velocity as well as a distinct reduction in the number of CSF flow jets (red), compared to the number of flow jets present in the symptomatic patient prior to treatment (FIG. 16a). In addition, average CSF velocity (average peak height) was reduced in the asymptomatic MS patient following treatment as compared to the symptomatic patient prior to treatment. CSF Flow was also more homogeneous (less peak height variation) in the asymptomatic patient than in the symptomatic patient. The CSF flow measurements obtained immediately following successful AO treatment of the patient and the cessation of her MS symptoms also exhibited a 28.6% reduction of the patient's measured CSF pressure gradient. The patient is currently being maintained free of MS symptoms (vertigo and vomiting on recumbency) by weekly treatments with the AO instrument.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention.

The invention claimed is:

1. A method of providing an indication of to multiple sclerosis in a patient using magnetic resonance imaging comprising the steps of:
    (a) using an upright magnetic resonance imaging apparatus, obtaining one or more measurements representing cerebrospinal fluid flow in the cervical spine of the patient in an upright position;
    (b) comparing the one or more measurements to one or more corresponding predetermined threshold values to determine if the cerebrospinal fluid flow measurement meets the at least one predetermined threshold value;

(c) using magnetic resonance imaging, detecting a presence of a cranio-cervical structural abnormality in the neck of the patient;

(d) using magnetic resonance imaging, detecting a presence of one or more peri-ventricular brain lesions in the patient; and (e) providing an indication of to multiple sclerosis based on the one or more measurements, the presence or absence of a cranio-cervical structural abnormality, and the presence of peri-ventricular brain lesions, wherein the combination of (i) one or more of the measurements not meeting the predetermined threshold value, (ii) the presence of a cranio-cervical structural abnormality, and (iii) the presence of peri-ventricular brain lesions, is indicative of to multiple sclerosis.

2. A method as recited in claim 1 wherein the comparing step includes determining if the one or more measurements demonstrate impeded cerebrospinal fluid flow, and the presence of one or more measurements demonstrating accelerated CSF flow is indicative of presence of to multiple sclerosis.

3. A method as recited in claim 1 wherein the comparing step includes determining the one or more measurements demonstrate accelerated cerebrospinal fluid flow, wherein a presence of one or more measurements demonstrating accelerated CSF flow is indicative of presence of to multiple sclerosis.

4. A method as recited in claim 1 further comprising measuring cerebrospinal fluid flow using magnetic resonance imaging while the patient is in a recumbent position.

5. A method as recited in claim 1 wherein the one or more measurements derived in the obtaining step include at least one value of cerebrospinal fluid velocity.

6. A method as recited in claim 5 wherein the at least one value of cerebrospinal fluid velocity includes at least one peak value of cerebrospinal fluid velocity.

7. A method as recited in claim 6 wherein the at least one peak value includes peak cerebrospinal fluid outflow velocity measured in an upright position.

8. A method as recited in claim 6 wherein the at least one peak value includes peak cerebrospinal fluid inflow velocity measured in an upright position.

9. A method as recited in claim 1 wherein the patient is a patient having a history of trauma to the head or neck.

10. A method as recited in claim 1 further comprising the step of treating the patient to reduce intracranial cerebrospinal fluid pressure if the one or more measurements is indicative of multiple sclerosis.

11. A method as recited in claim 10 wherein the treating step includes a treatment selected from the group consisting of stenting the azygous vein, stenting one or both of the internal jugular vein, and installation of a cerebrospinal fluid drainage shunt, and repair of an anatomical abnormality which impedes or accelerates cerebrospinal fluid flow.

12. A method as recited in claim 1 further comprising treating the patient to alleviate or retard development of MS if the one or more measurements is indicative of multiple sclerosis.

13. A method as recited in claim 1 further comprising further monitoring the patient to detect incipient MS if the one or more measurements demonstrate abnormal cerebrospinal fluid flow.

14. A method as recited in claim 1 wherein the cranio-cervical structural abnormality includes one or more abnormalities selected from the group consisting of cervical disc herniations and displacements; dislocations, fractures, and degeneration of cervical vertebrae; abnormal ligaments in the cervical spine; abnormalities of the lordotic curvature; displacements or distortion of the spinal cord; and cerebellar tonsil ectopia.

15. The method of claim 1, further comprising taking an image of the patient's cervical spine in the midline sagittal plane.

16. The method of claim 1, further comprising taking an image of the patient's cervical spine in the axial plane.

17. The method of claim 16, wherein the image is taken at the mid C-2 of the patient's cervical spine, perpendicular to the patient's spinal canal.

18. The method of claim 1, wherein the threshold value is a mean peak inflow velocity of about 0.55 cm/sec.

19. The method of claim 1, wherein the threshold value is a mean peak inflow velocity of about 0.5 cm/sec.

20. The method of claim 1, wherein the threshold value is a mean peak inflow velocity of about 0.34 cm/sec.

21. The method of claim 1, wherein the threshold value is a mean peak outflow velocity of about 1.4 cm/sec.

22. The method of claim 1, wherein the threshold value is a mean peak outflow velocity of about 1.1 cm/sec.

23. The method of claim 1, wherein the threshold value is a mean peak outflow velocity of about 0.77 cm/sec.

* * * * *